United States Patent
Bashan et al.

(10) Patent No.: US 10,335,546 B2
(45) Date of Patent: *Jul. 2, 2019

(54) APPARATUS FOR OPTIMIZING A PATIENT'S INSULIN DOSAGE REGIMEN

(71) Applicant: Hygieia, Inc., Ann Arbor, MI (US)

(72) Inventors: Eran Bashan, Ann Arbor, MI (US); Israel Hodish, Ann Arbor, MI (US)

(73) Assignee: Hygieia, Inc., Ann Arbor, MI (US)

( * ) Notice: Subject to any disclaimer, the term of this patent is extended or adjusted under 35 U.S.C. 154(b) by 488 days.

This patent is subject to a terminal disclaimer.

(21) Appl. No.: 14/067,479

(22) Filed: Oct. 30, 2013

(65) Prior Publication Data

US 2014/0094745 A1    Apr. 3, 2014

Related U.S. Application Data

(63) Continuation of application No. 12/417,955, filed on Apr. 3, 2009, now Pat. No. 8,600,682.

(Continued)

(51) Int. Cl.
*G01N 33/48* (2006.01)
*A61M 5/172* (2006.01)
(Continued)

(52) U.S. Cl.
CPC ....... *A61M 5/1723* (2013.01); *A61B 5/14532* (2013.01); *G06F 19/3456* (2013.01);
(Continued)

(58) Field of Classification Search
None
See application file for complete search history.

(56) References Cited

U.S. PATENT DOCUMENTS

| 4,403,984 A | 9/1983 | Ash et al. |
| 4,731,726 A | 3/1988 | Allen, III |

(Continued)

FOREIGN PATENT DOCUMENTS

| WO | WO 03/065033 | * 8/2003 | ............ G01N 33/48 |
| WO | 2005/072792 | 8/2005 | |

(Continued)

OTHER PUBLICATIONS

Ryff-de Lèche, Arnika et al. "Clinical Application of Two Computerized Diabetes Management Systems: Comparison with the Log-Book Method," *Diabetes Research*, 19 (1992) 97-105.

(Continued)

*Primary Examiner* — Larry D Riggs, II
(74) *Attorney, Agent, or Firm* — Jones Day

(57) ABSTRACT

An apparatus for optimizing a patient's insulin dosage regimen over time, comprising: at least a first computer-readable memory for storing data inputs corresponding at least to one or more components in a patient's present insulin dosage regimen and the patient's blood-glucose-level measurements determined at a plurality of times; a processor operatively connected to the at least first computer-readable memory, the processor programmed at least to determine from the data inputs corresponding to the patient's blood-glucose-level measurements determined at a plurality of times whether and by how much to vary at least one of the one or more components of the patient's present insulin dosage regimen in order to maintain the patient's future blood-glucose-level measurements within a predefined range; and a display operative to display information corresponding to at least the patient's present insulin dosage regimen.

23 Claims, 10 Drawing Sheets

Related U.S. Application Data

(60) Provisional application No. 61/060,645, filed on Jun. 11, 2008, provisional application No. 61/042,487, filed on Apr. 4, 2008.

(51) Int. Cl.
*A61B 5/145* (2006.01)
*G06F 19/00* (2018.01)
*A61B 5/00* (2006.01)
*A61M 5/142* (2006.01)

(52) U.S. Cl.
CPC ........ *G06F 19/3468* (2013.01); *A61B 5/0002* (2013.01); *A61M 5/142* (2013.01)

(56) References Cited

U.S. PATENT DOCUMENTS

| | | |
|---|---|---|
| 4,981,779 A | 1/1991 | Wagner |
| 5,216,597 A | 6/1993 | Beckers |
| 5,251,126 A | 10/1993 | Kahn et al. |
| 5,822,715 A * | 10/1998 | Worthington .......... G09B 19/00 235/375 |
| 5,956,501 A | 9/1999 | Brown |
| 6,024,699 A | 2/2000 | Surwit et al. |
| 6,186,145 B1 | 2/2001 | Brown |
| 6,233,539 B1 | 5/2001 | Brown |
| 6,379,301 B1 | 4/2002 | Worthington et al. |
| 6,540,672 B1 | 4/2003 | Simonsen et al. |
| 6,544,212 B2 | 4/2003 | Galley et al. |
| 6,560,471 B1 * | 5/2003 | Heller .................. A61B 5/0002 600/309 |
| 6,565,114 B1 | 5/2003 | Thomas |
| 6,572,542 B1 | 6/2003 | Houben et al. |
| 6,575,905 B2 | 6/2003 | Knobbe et al. |
| 6,656,114 B1 | 12/2003 | Poulsen et al. |
| 6,669,663 B1 | 12/2003 | Thompson |
| 6,740,072 B2 | 5/2004 | Starkweather et al. |
| 6,923,763 B1 | 8/2005 | Kovatchev et al. |
| 7,025,425 B2 | 4/2006 | Kovatchev et al. |
| 7,060,059 B2 | 6/2006 | Keith et al. |
| 7,108,680 B2 | 9/2006 | Rohr et al. |
| 7,137,951 B2 | 11/2006 | Pilarski |
| 7,167,818 B2 | 1/2007 | Brown |
| 7,204,823 B2 | 4/2007 | Estes et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,404,796 B2 | 7/2008 | Ginsberg |
| 7,509,156 B2 | 3/2009 | Flanders |
| 7,553,281 B2 | 6/2009 | Hellwig et al. |
| 7,651,845 B2 | 1/2010 | Doyle et al. |
| 7,734,323 B2 | 6/2010 | Blomquist |
| 7,853,455 B2 | 12/2010 | Brown |
| 7,877,271 B2 | 1/2011 | Brown |
| 7,901,625 B2 | 3/2011 | Brown |
| 7,904,310 B2 | 3/2011 | Brown |
| 7,912,688 B2 | 3/2011 | Brown |
| 7,920,998 B2 | 4/2011 | Brown |
| 7,949,507 B2 | 5/2011 | Brown |
| 2003/0028089 A1 | 2/2003 | Galley et al. |
| 2003/0050621 A1 | 3/2003 | Lebel et al. |
| 2003/0163088 A1* | 8/2003 | Blomquist .......... G06F 19/3412 604/131 |
| 2004/0042272 A1 | 3/2004 | Kurata |
| 2004/0044272 A1 | 3/2004 | Moeman et al. |
| 2004/0054263 A1 | 3/2004 | Moerman et al. |
| 2005/0049179 A1 | 3/2005 | Davidson et al. |
| 2005/0055010 A1 | 3/2005 | Pettis et al. |
| 2005/0177398 A1 | 5/2005 | Watanabe et al. |
| 2005/0171503 A1 | 8/2005 | Van Den Berghe et al. |
| 2005/0192494 A1 | 9/2005 | Ginsberg |
| 2005/0192557 A1 | 9/2005 | Brauker et al. |
| 2005/0197533 A1 | 9/2005 | May et al. |
| 2005/0197621 A1 | 9/2005 | Poulsen et al. |
| 2005/0272640 A1 | 12/2005 | Doyle, III et al. |
| 2006/0047192 A1 | 3/2006 | Hellwig et al. |
| 2006/0160722 A1 | 7/2006 | Green et al. |
| 2006/0173260 A1 | 8/2006 | Gaoni et al. |
| 2006/0224109 A1 | 10/2006 | Steil et al. |
| 2006/0264886 A9 | 11/2006 | Pettis et al. |
| 2007/0078314 A1 | 4/2007 | Grounsell et al. |
| 2007/0078818 A1 | 4/2007 | Zivitz et al. |
| 2007/0168224 A1 | 7/2007 | Letzt et al. |
| 2007/0232876 A1* | 10/2007 | Otto .................. G06F 19/3456 600/365 |
| 2007/0293742 A1 | 12/2007 | Simonsen et al. |
| 2008/0097289 A1 | 4/2008 | Steil et al. |
| 2008/0119705 A1 | 5/2008 | Patel et al. |
| 2008/0139907 A1 | 6/2008 | Rao et al. |
| 2008/0172030 A1 | 7/2008 | Blomquist |
| 2008/0214919 A1 | 9/2008 | Harmon et al. |
| 2008/0269585 A1 | 10/2008 | Ginsberg |
| 2009/0069636 A1 | 3/2009 | Zivitz et al. |
| 2009/0247982 A1 | 10/2009 | Krulevitch et al. |
| 2009/0253970 A1 | 10/2009 | Bashan |
| 2009/0253973 A1 | 10/2009 | Bashan |
| 2009/0299152 A1 | 12/2009 | Taub et al. |
| 2010/0016700 A1 | 1/2010 | Sieh et al. |
| 2010/0124996 A1 | 5/2010 | Lindsay |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0256047 A1 | 10/2010 | Sieh et al. |
| 2010/0305545 A1 | 12/2010 | Kanderian et al. |
| 2010/0331652 A1 | 12/2010 | Groll et al. |
| 2010/0331654 A1 | 12/2010 | Jerdonek et al. |

FOREIGN PATENT DOCUMENTS

| | | |
|---|---|---|
| WO | 2005/110222 | 11/2005 |
| WO | 2007/116226 | 10/2007 |
| WO | 2009/146119 | 12/2009 |
| WO | 2009/146121 | 12/2009 |
| WO | 2010/056718 | 5/2010 |
| WO | 2010/075350 | 7/2010 |
| WO | 2010/089304 | 8/2010 |
| WO | 2010/089305 | 8/2010 |
| WO | 2010/089306 | 8/2010 |
| WO | 2010/089307 | 8/2010 |

OTHER PUBLICATIONS

Hirsch, Irl B. et al. "Clinical Application of Emerging Sensor Technologies in Diabetes Management: Consensus Guidelines for Continuous Glucose Monitoring (CGM)," *Diabetes Technology & Therapeutics*, 10:4 (2008) 232-244.

Schrezenmeir, J. et al. "Computer Assisted Insulin Dosage Adjustment—Perspectives for Diabetes Control," 1990.

Lehmann, E. D. et al. "Insulin Dosage Adjustment in Diabetes," *J Biomed Eng*, 14 (May 1992) 243-249.

Lehmann, E. D. et al. "Application of Computers in Diabetes Care—A Review, I. Computers for Data Collection and Interpretation," *Med Inform*, 20:4 (1995) 281-302.

Lehmann, E. D. et al. "Application of Computers in Diabetes Care—A Review, II. Computers for Decision Support and Education," *Med Inform*, 20:4 (1995) 303-329.

Lehmann, E. D. et al. "Retrospective Validation of a Physiological Model of Glucose-Insulin Interaction in Type 1 Diabetes Mellitus," *Med Eng Phys*, 16 (May 1994) 193-202.

Jenkins, Alicia J. et al. "Evaluation of an Algorithm to Guide Patients with Type 1 Diabetes Treated with Continuous Subcutaneous Insulin Infusion on How to Respond to Real-Time Continuous Glucose Levels," *Diabetes Care*, 33:6 (Jun. 2010) 1242-1248.

Charpentier, Guillaume et al. "The Diabeo Software Enabling Individualized Insulin Dose Adjustments Combined with Telemedicine Support Improves HbA$_{1c}$ in Poorly Controlled Type 1 Diabetic Patients," *Diabetes Care* (online: care.diabetesjournals.org)(Jan. 25, 2011) 1-7.

Mulvaney, Shelagh A. et al. "An Internet-Based Program to Improve Self-Management in Adolescents with Type 1 Diabetes," *Diabetes Care*, 33:3 (Mar. 2010) 602-604.

(56) References Cited

OTHER PUBLICATIONS

Strange, Poul "Treat-to-Target Insulin Titration Algorithms When Initiating Long or Intermediate Acting Insulin in Type 2 Diabetes," *Journal of Diabetes Science and Technology*, 1:4 (Jul. 2007) 540-548.

The Juvenile Diabetes Research Foundation Continuous Glucose Monitoring Study Group "Continuous Glucose Monitoring and Intensive Treatment of Type 1 Diabetes," *N Eng J Med*, 359 (2008) 1-13.

Renard, Eric "Clinical Experience with an Implanted Closed-Loop Insulin Delivery System," *Arq Bras Endrocrinol Metab*, 52:2 (2008) 349-354 (with English Abstract).

Berger, M. et al. "Computer Programs to Assist the Physician in the Analysis of Self-Monitored Blood Glucose Data," Nov. 1988, 52-57.

Oyer, David S. "Aic Control in a Primary Care Setting: Self-Titrating an Insulin Analog Pre-Mix (INITIATEplus Trial)," *Am J Med*, 122:11 (Nov. 2009) 1043-1049.

Stone, Roslyn A. et al. "Active Care Management Supported by Home Telemonitoring in Veterans with Type 2 Diabetes," *Diabetes Care*, 33:3 (Mar. 2010) 478-484.

Quinn, Charlene C. et al. "Cluster-Randomized Trial of a Mobile Phone Personalized Behavioral Intervention for Blood Glucose Control," *Diabetes Care* (online: care.diabetesjournals.org)(Jul. 25, 2011) 1-9.

Bergenstal, Richard M. et al. "Effectiveness of Sensor-Augmented Insulin-Pump Therapy in Type 1 Diabetes," *N Eng J Med*, 363:4 (Jul. 22, 2010) 311-320.

Miller, Shahar et al. "Automatic Learning Algorithm for the MD-Logic Artificial Pancreas System," *Diabetes Technology & Therapeutics*, 13:10 (2011) 1-8.

Kilbride, Lynn et al. "Managing Blood Glucose During and After Exercise in Type 1 Diabetes: Reproducibility of Glucose Response and a Trial of a Structured Algorithm Adjusting Insulin and Carbohydrate Intake," *Journal of Clinical Nursing* (2011) 1-7.

Campos-Cornejo, Fabiola et al. "An Advisory Protocol for Rapid- and Slow-Acting Insulin Therapy Based on a Run-to-Run Methodology," *Diabetes Technology & Therapeutics*, 12:7 (2010) 555-565.

International Search Report for PCT/US2009/039418 dated Nov. 17, 2009.

International Search Report for PCT/US2009/063989 dated May 28, 2010.

International Search Report for PCT/US2010/055246 dated Dec. 13, 2010.

International Search Report for PCT/US2009/039421 dated Nov. 17, 2009.

Holman, et al. "Addition of Biphasic, Prandial, or Basal Insulin to Oral Therapy in Type 2 Diabetes", The New England Journal of Medicine, vol. 357(17), pp. 1716-1730; 2007.

Herman et al., "A clinical Trial of Continuous Subcutaneous Insulin Infusion Versus Multiple Daily Injections in Older Adults with Type 2 Diabetes", Diabetes Care, vol. 28(7) pp. 1568-1573; 2005.

Bergenstal, et al., "Adjust toTarget in Type 2 Diabetes", Diabetes Care, vol. 31(7), pp. 1305-1310; 2008.

Albisser, A. Michael, "Toward Algorithms in Diabetes Self-Management", Diabetes Technology & Therapeutics, vol. 5(3), pp. 371-373; 2003.

Albisser, A.M., "Devices for the Control of Diabetes Mellitus", Proceedings of the IEEE, vol. 67(9), pp. 1308-1320; 1979.

Albisser, et al., "Insulin dosage adjustment using manual methods and computer algorithms: a comparative study", Medical & Biological Engineering & Computing, vol. 24, pp. 577-587; 1986.

Albisser, et al., "Intelligent Instrumentation in Diabetic Management", Critical Reviews in Biomedical Engineering, vol. 17(1), pp. 1-24; 1989.

Albisser, A.M., "The Role(s) of glucose Sensing in Diabetes: Informative, Archival, or Control?", Annual International Conference of the IEEE Engineering Medicine and Biological Society, vol. 12(2), pp. 0474-0475; 1990.

Meneghini, et al., "An Electronic Case Manager for Diabetes Control", Diabetes Care, vol. 21(4), pp. 591-596. 1998.

Ambrosiadou, et al., "Clinical Evaluation of the Diabetes expert system for decision support by multiple regiment insulin dose adjustment", Computer Methods and Programs in Biomedicine, vol. 49, pp. 105-115; 1996.

Andreassen, et al., "A probabilistic approach to glucose prediction and insulin dose adjustment: description of metabolic model and pilot evaluation study", Computer Methods and programs in Biomedicin, vol. 41, pp. 153-165; 1996.

Balas, et al, "Computerized Knowledge Management in Diabetes Care", Medical Care, vol. 42(6), pp. 610-621; 1994.

Raskin, et al., "Basal insulin or premix analogue therapy in type 2 diabetes patients", European Journal of Medicine, vol. 18, pp. 56-62; 2007.

Berger, et al, "Computer Programs to Assist the Physician in the Analysis of Self-Monitored Blood Glucose Data", Laboratory of Theoretical and Physical Biology, National Institutes of Child Health and Human Development, National Institutes of Health, Bethesda, MD, pp. 52-57.

Brahams, et al, "Medicine and the Law—Decision Aids and the Law", The Lancet, pp. 632-634; 1989.

Bu, et al, "Benefits of Information Technology-Enabled Diabetes Management", Diabetes Care, vol. 30(5), pp. 1137-1142; 2007.

Buse, et al, "DURAbility of Basal Versus Lispro Mix 75/25 Insulin Efficacy. (DURABLE) Trial24-Week Results", Diabetes Care, vol. 32(6), pp. 1007-1013; 2009.

Chiarelli, et al, "Controlled Study in Diabetic Children Comparing Insulin-Dosage Adjustment by Manual and Computer Algorithms", Diabetes Care, vol. 13(10), pp. 1080-1088; 1990.

Janka, et al, "Comparison of BasalInsulin Added to Oral Agents Versus Twice-Daily Premixed Insulin as Initial Insulin Therapy for Type 2 Diabetes", Diabetes Care, vol. 28(2), pp. 254-259; 2005.

Day, J.P., "Some considerations of legal liability concerning the use and future development of knowledge based or expert systems in diabetes care", Diab. Nutr. Metab., vol. 8, pp. 195-200; 1995.

Deutsch, et al, "Computer-assisted diabetic management: a complex approach", Computer Methods and Programs in Biomedicine, vol. 32, pp. 195-214; 1990.

Deutsch, et al, "Time series analysis and control of blood glucose levels in diabetic patients", ComputerMethods and Programs in Biomedicine, vol. 41, pp. 167-182; 1994.

Deutsch, et al, "UTOPIA: a consultation system for visit-by-visit diabetes managment", Med. Inform., vol. 21(4), pp. 345-358; 1996.

Barnett, Anthony, "Dosing of Insulin Glargine in the Treatment of Type 2 Diabetes", ClinicalTherapeutics, vol. 29(6), pp. 987-999; 2007.

Dall, et al, "Economic Costs of Diabetes in the U.S. in 2007", Diabetes Care, vol. 31(3), pp. 596-615; 2008.

Albisser, et al, "Electronics and the Diabetic", IEEE Transactions on Biomedical Engineering, vol. BME-29(4), pp. 239-248; 1982.

European Diabetes Policy Group 1998, "A desktop guide to Type I (insulin-dependent) diabetes mellitus", Diabetic Medicine, vol. 16, pp. 253-266; 1999.

European Diabetes Policy Group 1999, "A desktop guide to Type 2 diabetes mellitus" Diabetic Medicine, vol. 16, pp. 716-730; 1999.

Farmer, et at, "A Randomized Controlled Trial of the Effect of Real-Time Telemedicine Support on Glycemic Control in Young Adults With Type 1 Diabetes (ISRCTN 46889446)", Diabetes Care, vol. 28(11), pp. 2697-2702; 2005.

Ford, et al, "Trends in A1C Concentrations Among U.S. Adults with Diagnosed Diabetes From 1999 to 2004", DiabetesCare, vol. 31(1), pp. 102-104; 2008.

Van Herpe, et al, "Glycemic penalty index for adequately assessing and comparing different blood glucose control algorithms", Critical Care, vol. 12(R24), pp. 1-14; 2008.

Hayes, et al, "Primary care physician beliefs about insulin initiation in patients with type 2 diabetes". Int J Clin Pract., vol. 62(6), pp. 860-868; 2008.

Hermanyi, et al, "Management of diabetics with the use of a microprocessor. Comparison of insulin treatments based on blood and urine glucose levels", Acta Diabetol. Lat.. vol. 25, pp. 33-40; 1988.

(56) References Cited

OTHER PUBLICATIONS

Hirsch, et al, "A Real-World Approach to Insulin Therapy in Primary Care Practice", Clinical Diabetes, vol. 23(2), pp. 78-86; 2005.
Hoerger, et al, "Is Glycemic Control Improving in U.S. Adults?", Diabetes Care, vol. 31(1), pp. 81-86; 2008.
Kennedy, et al, "Impact of Active Versus Usual Algorithmic Titration of Basal Insulin and Point-of-Care Versus Laboratory Measurement of HbA1c on Glycemic Control in Patients With Type 2 Diabetes", Diabetes Care, vol. 29(1), pp. 1-8; 2006.
Davies, et al, "Improvement of Glycemic Control in Subjects With Poorly Controlled Type 2 Diabetes", Di betes Care, vol. 28(6), pp. 1282-1288; 2005.
Saaddine, et al, Improvements in Diabetes Processes of Care and Intermediate Outcomes: United States, 1988-2002; Ann Intern Med., vol. 144, pp. 465-474; 2006.
Gomis, et al, "Improving metabolic control in sub-optimally controlled subjects with Type 1 diabetes: Comparison of two treatment algorithms using insulin glargine", Diabetes Research and Clinical Practice, vol. 77, pp. 84-91; 2007.
Davies, et al, "Initiation of insulin glargine in suboptimally controlled patients with type 2 diabetes: sub-analysis of AT. LANTUS trial comparing treatment outcomes in subjects from primary and secondary care in the UK", Diabetes, Obesity and Metabolism, vol. 9, pp. 706-713; 2007.
Davies, et al, "Initiation of insulin glargine therapy in type 2 diabetes subjects suboptimally controlled on oral antidiabetic agents: results from the AT.LANUTS trial", Diabetes, Obesity and Metabolism, vol. 10, pp. 387-399; 2008.
Mayfield, et al, "Insulin Therapy for Type 2 Diabetes: Rescue, Augmentation, and Replacement of Beta-Cell Function", Am Fam Physician, vol. 70, pp. 489-500, 511-512; 2004.
Koro, et al, Glycemic Control From 1988 to 2000 Among U.S. Adults Diagnosed With Type 2 Diabetes, Diabetes Care, vol. 27(1), pp. 17-20; 2004.
Guier, et al, "Intensification lessons with modem premixes: From clinical trial to clinical practice", Diabetes Research and Clinical Practice, vol. 81S, pp. S23-S30; 2008.
Lehmann, et al, "Application of computers in diabetes care—a review. II. Computers for decision support and education", Med. Inform., vol. 20(4), pp. 303-329; 1995.
Lehmann, et al, "Compartmental models for glycaemic prediction and decision-support in clinical diabetes care: promise and reality", Computer Methods and Programs in Biomedicine, vol. 56, pp. 193-204; 1998.
Lougheed, et al, "Stabilizing Blood Glucose with a Novel Medical Expert System", Blosensors, vol. 3, pp. 381-389; 1987/1988.
Spellman, Craig, "Management of Diabetes in the Real World: Tight Control of Glucose Metabolism", JAOA, vol. 103 (8), Supplement 5, pp. S8-S13; 2003.
Miyako, et al, "Improved diabetes controlby using 'close adjustment algorithms'", Pediatrics International, vol. 46, pp. 678-684; 2004.
Nathan, et al, "Management of Hyperglycemia in Type 2 Diabetes: A Consensus Algorithm for the Initiation and Adjustment of Therapy", Diabetes Care, vol. 29(8), pp. 1963-1972; 2006.
Nathan, et al, "Medical Management of Hyperglycemia in Type 2 Diabetes: A Consensus Algorithm for the Initiation and Adjustment of Therapy", Diabetes Care, vol. 31(12), pp. 1-11; 2008.
Marshall, et al, "New Microprocessor-Based Insulin Controller", IEEE Transactions of Biomedical Engineering, vol. BME-30(11), pp. 689-695; 1983.
Bretzel, et al, "Once-daily basal insulin glarglne versus thrice-daily prandial insulin lispro in people with type 2 diabetes on oral hypoglycaemic agents (APPOLO): an open randomised controlled trial", The Lancet, vol. 371, pp. 1073-1084; 2008.
Woodcock, et al, "Patient concerns in their first year with Type 2 diabetes: Patient and practice nurse views", Patient Education and Counseling, vol. 42, pp. 257-270; 2001.
Pemick, et al, "Personal Computer Programs to Assist with Self-Monitoring of Blood Glucose and Self-Adjustment of Insulin Dosage", Diabetes Care, vol. 9(1), pp. 61-69; 1986.
Peterson, et al, "Randomized Trial of Computer-Assisted Insulin Delivery in Patients with Type I Diabetes Beginning Pump Therapy", The American Journal of Medicine, vol. 81, pp. 69-72; 1986.
Choe, et al, "Proactive Case Management of High-risk Patients With Type 2 Diabetes Mellitus by a Clinical Pharmacist: A Randmized Controlled Trial", The American Journal of Managed Care, vol. 11(4), pp. 253-260; 2005.
ACCORD Protocol—Action to Control Cardiovascular Risk in Diabetes, May 11, 2005.
Queale, et al, "Glycemic Control and Sliding Scale Insulin Use in Medical Inpatients Wth Diabetes Mellitus", Arch Intern Med, vol. 157, pp. 545-552; 1997.
Ray, et al, "Effect of intensive control of glucose on cardiovascular outcomes and death in patients with diabetes mellitus: a meta-analysis of randomised controlled trials", The Lancet, vol. 373, pp. 1765-1772; 2009.
Spoelstra, et al, "Refill compliance in type 2 diabetes mellitus: a predictor of switching to insulin therapy?" Pharmcoepldemiology and Drug Safety, vol. 12, pp. 121-127; 2003.
Schiffrin, et al, "Computer-assisted Insulin Dosage Adjustment", Diabetes Care, vol. 8(6), pp. 545-552; 1985.
Schrezenmeir, et al, "Computer Assisted Insulin Dosage Adjustment—Perspectives for Diabetes Control", Abteilung fur Innere Medizin—Endokrinologie, III. Medizinische Klinik and Poliklinik, Johannes Gutenberg-Universitat, Mainz, Germany; pp. 116-123.
Schulz, et al, "Diabetes Self-Adjustment by a Computerized Program—First Experiences in Inpatient and Outpatient Treatment", Dept. of Endocrinology, Dept. of Physiology, University of Mainz, Langenbeckstrasse, Germany, pp. 578-582.
Albisser, A. Michael, "Six generations of the insulin dosage computer: A new clinical device for diabetes self-management through specialized centres", AnnualInternational Conference of the IEEE Engineering in Medicine and Biology Society, vol. 12(3), pp. 0996-0997; 1990.
Skyler, et al, "Algorithms for Adjustment of Insulin Dosage by Patients Who Monitor Blood Glucose", Diabetes Care, vol. 4(2), pp. 311-318; 1981.
Stratton, et al, "Association of glycaemia with macrovascular and microvascular complications of type 2 diabetes (UKPDS 35): prospective observational study", BMJ, vol. 321, pp. 405-412; 2000.
Dinsmoor, RobertS., "The Artifical Pancreas—How to close the loop", JDRF Countdown, Wnter 2007, pp. 24-25.
Farmer, et al, "The future of open- and closed-loop insulin delivery systems", JPP, vol. 60, pp. 1-13; 2007.
Cramer, et al, "The significance of compliance and persistence in the treatment of diabetes, hypertension and dyslipidaemia: a review", Int. J. Clin. Pract.,vol. 62(1), pp. 76-87; 2008.
Meneghinl, et al, "The usage of a simplified self-titration dosing guideline (303 Algorithm) for Insulin determir in patients with type 2 diabetes—results of the randomized, controlled PREDICTIVE 303 study", Diabetes, Obesity and Metabolism, vol. 9, pp. 902-931; 2007.
Eliaschewitz, et al, "Therapy in Type 2 Diabetes: Insulin Glargine vs. NPH Insulin Both in Combination with Glimepirlde", Archives of Medical Research, vol. 37, pp. 495-501; 2006.
Buse, et al, The DURABLE Trial 24-week Results.
Nathan, et al, "Translating the A1C Assay Into Estimated Average Glucose Values", Diabetes Care, vol. 31(8) pp. 1-6; 2008.
Ambrosiadou, et al, "Clinical Evaluation of the DIABETES expert system for decision support by multiple regimen insulin dose adjustment", Computer Methods and Programs in Biomedicine, vol. 49, pp. 105-115; 1996.
Hirsch, et al, "Self-Monitoring of Blood Glucose (SMBG) in Insulin- and Non-Insulin-Using Adults with Diabetes: Consensus Recommendations for Improving SMBG Accuracy, Utilization and Research", Diabetes Technology & Therapeutics, vol. 10(6), pp. 419-440; 2008.

(56) References Cited

OTHER PUBLICATIONS

Aubert, et al, "Nurse Case Mangement to Improve Glycemic Control in Diabetic Patients in a Health Maintenance Organization", vol. 129(8), pp. 605-612; 1998.

* cited by examiner

APPARATUS FOR OPTIMIZING A PATIENT'S INSULIN DOSAGE REGIMEN

RELATED APPLICATIONS

This application is a continuation of U.S. application Ser. No. 12/417,955, filed 3 Apr. 2009, and claims the benefit of priority from, U.S. provisional application Ser. No. 61/042,487, filed 4 Apr. 2008, and U.S. provisional application Ser. No. 61/060,645, filed 11 Jun. 2008. Each of these applications, are incorporated herein by reference in their entireties.

FIELD OF THE INVENTION

The present invention relates to an apparatus for optimizing the insulin dosage regimen for a diabetes patient, and more particularly to such an apparatus comprising a processor programmed at least to determine from the data inputs corresponding to the patient's blood-glucose-level measurements determined at a plurality of times whether and by how much to vary at least one of the one or more components of the patient's present insulin dosage regimen in order to maintain the patient's future blood-glucose-level measurements within a predefined range.

BACKGROUND

Diabetes is a chronic disease resulting from deficient insulin secretion by the endocrine pancreas. About 7% of the general population in the Western Hemisphere suffers from diabetes. Of these persons, roughly 90% suffer from Type-2 diabetes while approximately 10% suffer from Type-1. In Type-1 diabetes, patients effectively surrender their endocrine pancreas to autoimmune distraction and so become dependent on daily insulin injections to control blood-glucose-levels. In Type-2 diabetes, on the other hand, the endocrine pancreas gradually fails to satisfy increased insulin demands, thus requiring the patient to compensate with a regime of oral medications or insulin therapy. In the case of either Type-1 or Type-2 diabetes, the failure to properly control glucose levels in the patient may lead to such complications as heart attacks, strokes, blindness, renal failure, and even premature death.

Insulin therapy is the mainstay of Type-1 diabetes management and one of the most widespread treatments in Type-2 diabetes, about 27% of the sufferers of which require insulin. Insulin administration is designed to imitate physiological insulin secretion by introducing two classes of insulin into the patient's body: Long-acting insulin, which fulfills basal metabolic needs; and short-acting insulin (also known as fact-acting insulin), which compensates for sharp elevations in blood-glucose-levels following patient meals. Orchestrating the process of dosing these two types of insulin, in whatever form (e.g., separately or as premixed insulin) involves numerous considerations.

First, patients measure their blood-glucose-levels (using some form of a glucose meter) on average about 3 to 4 times per day. The number of such measurements and the variations therebetween complicates the interpretation of these data, making it difficult to extrapolate trends therefrom that may be employed to better maintain the disease. Second, the complexity of human physiology continuously imposes changes in insulin needs for which frequent insulin dosage regimen adjustments are warranted. Presently, these considerations are handled by a patient's endocrinologist or other healthcare professional during clinic appointments. Unfortunately, these visits are relatively infrequent—occurring once every 3 to 6 months—and of short duration, so that the physician or other healthcare professional is typically only able to review the very latest patient medical data. In consequence, it has been shown that more than 60% of patients control their diabetes at sub-optimal levels, leading to unwanted complications from the disease.

Indeed, one of the major obstacles of diabetes management is the lack of availability of a patient's healthcare professional and the relative infrequency of clinic appointments. Studies have, in fact, established that more frequent insulin dosage regimen adjustments—e.g., every 1 to 2 weeks—improves diabetes control in most patients. Yet as the number of diabetes sufferers continues to expand, it is expected that the possibility of more frequent insulin dosage regimen adjustments via increased clinic visits will, in fact, decrease. And, unfortunately, conventional diabetes treatment solutions do not address this obstacle.

The device most commonly employed in diabetes management is the glucose meter. Such devices come in a variety of forms, although all are characterized by their ability to provide patients near instantaneous readings of their blood-glucose-levels. This additional information can be used to better identify dynamic trends in blood-glucose-levels. However, all conventional glucose meters are designed to be diagnostic tools rather than therapeutic ones. Therefore, by themselves, even state-of-the-art glucose meters do not lead to improved glycemic control.

One conventional solution to the treatment of diabetes is the insulin pump. Insulin pumps are devices that continuously infuse short acting insulin into a patient at a predetermined rate to cover both basal needs and meals. As with manual insulin administration therapy, a healthcare professional sets the pump with the patient's insulin dosage regimen during clinic visits. In addition to their considerable current expense, which prohibits their widespread use by patients with Type-2 diabetes, insulin pumps require frequent adjustment by the physician or other healthcare professional to compensate for the needs of individual patients based upon frequent blood-glucose-level measurements.

An even more recent solution to diabetes treatment seeks to combine an insulin pump and near-continuous glucose monitoring in an effort to create, in effect, an artificial pancreas regulating a patient's blood-glucose-level with infusions of short-acting insulin. According to this solution, real-time patient information is employed to match insulin dosing to the patient's dynamic insulin needs irrespective of any underlying physician-prescribed treatment plan. While such systems address present dosing requirements, they are entirely reactive and not instantaneously effective. In consequence of these drawbacks, such combined systems are not always effective at controlling blood glucose levels. For instance, such combined units cannot forecast unplanned activities, such as exercise, that may excessively lower a patient's blood-glucose level. And when the hypoglycemic condition is detected, the delay in the effectiveness of the insulin occasioned not only by the nature of conventional synthetic insulin but also the sub-dermal delivery of that insulin by conventional pumps results in inefficient correction of the hypoglycemic event.

While the foregoing solutions are beneficial in the management and treatment of diabetes in some patients, or at least hold the promise of being so, there continues to exist the need for means that would cost-effectively improve diabetes control in patients.

SUMMARY OF THE INVENTION

According to the specification, there are disclosed several embodiments of an apparatus for optimizing a patient's insulin dosage regimen over time, the apparatus comprising: at least a first computer-readable memory for storing data inputs corresponding at least to one or more components in a patient's present insulin dosage regimen and the patient's blood-glucose-level measurements determined at a plurality of times; a processor operatively connected to the at least first computer-readable memory, the processor programmed at least to determine from the data inputs corresponding to the patient's blood-glucose-level measurements determined at a plurality of times whether and by how much to vary at least one of the one or more components of the patient's present insulin dosage regimen in order to maintain the patient's future blood-glucose-level measurements within a predefined range; and a display operative to display information corresponding to at least the patient's present insulin dosage regimen.

According to a further feature, the apparatus may comprise a glucose meter operative to provide to the at least first computer-readable memory device the data inputs corresponding at least to the patient's blood-glucose-level measurements determined at a plurality of times. Further according to this feature, the processor may be operative to associate with the data inputs corresponding at least to the patient's blood-glucose-level measurements determined at a plurality of times an identifier indicative of when the measurement was input into the memory. Furthermore, there may be provided data entry means enabling a user to define the identifier associated with each blood-glucose-level measurement data-input, to confirm the correctness of the identifier associated with each blood-glucose-level measurement data-input, and/or to modify the identifier associated with each blood-glucose-level measurement data-input.

The inventive apparatus may further comprise an insulin pump, in addition to or instead of a glucose meter. According to this feature, the insulin pump is operatively connected to the processor and operative to deliver insulin to a patient according to the patient's present insulin dosage regimen. The insulin pump may further be operative to provide to the at least first computer-readable memory data inputs corresponding to the rate at which insulin is delivered to the patient by the pump according to the patient's present insulin dosage regimen.

According to one feature, the apparatus may comprise data entry means, operatively connected to the memory, for entering into the at least first memory device the data inputs corresponding to at least one of the one or more components of the patient's present insulin dosage regimen and the patient's blood-glucose-level measurements determined at a plurality of times.

Per another feature of the invention, the data inputs may further comprise data inputs corresponding to the patient's weight. According to this feature, the data entry means facilitate entering into the at least first memory the data inputs corresponding to the patient's weight.

Per yet another feature, data inputs may further comprise data inputs corresponding to the foods consumed by a patient. Accordingly, the data entry means facilitate entering into the at least first memory data inputs corresponding to the foods consumed by a patient, while the processor is operative to determine from the data inputs corresponding to the foods consumed by a patient the number of carbohydrates associated those foods.

Per still a further feature, the data inputs further comprise data inputs corresponding to the number of insulin units administered by a patient on a periodic basis. According to this feature, the data entry means facilitate entering into the at least first memory data inputs corresponding to the said number of insulin units administered by a patient.

BRIEF DESCRIPTION OF THE DRAWINGS

For a better understanding of the present invention and to show more clearly how it may be carried into effect, reference will now be made, by way of example, to the accompanying drawings, which show exemplary embodiments of the present invention, and in which.

DETAILED DESCRIPTION

As required, detailed descriptions of exemplary embodiments of the present invention are disclosed herein. However, it is to be understood that the disclosed embodiments are merely exemplary of the invention, which may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a providing a representative basis for teaching one skilled in the art to variously employ the present invention.

Turning now to the drawings, wherein like numerals refer to like or corresponding parts throughout the several views, the present invention comprehends an apparatus for optimizing the insulin dosage regimen in diabetes patients over time—such as in between clinic visits—to thereby enhance diabetes control.

As used herein, the term "insulin dose" means and refers to the quantity of insulin taken on any single occasion, while the term "insulin dosage regimen" refers to and means the set of instructions (typically defined by the patient's physician or other healthcare professional) defining when and how much insulin to take in a given period of time and/or under certain conditions. One conventional insulin dosage regimen, comprises several components, including a long-acting insulin dosage component, a plasma glucose correction factor component, and a carbohydrate ratio component. Thus, for instance, an exemplary insulin dosage regimen for a patient might be as follows: 25 units of long acting insulin at bedtime; 1 unit of fast-acting insulin for every 10 grams of ingested carbohydrates; and 1 unit of fast-acting insulin for every 20 mg/dL by which a patient's blood glucose reading exceeds 120 mg/dL.

Figure 1:
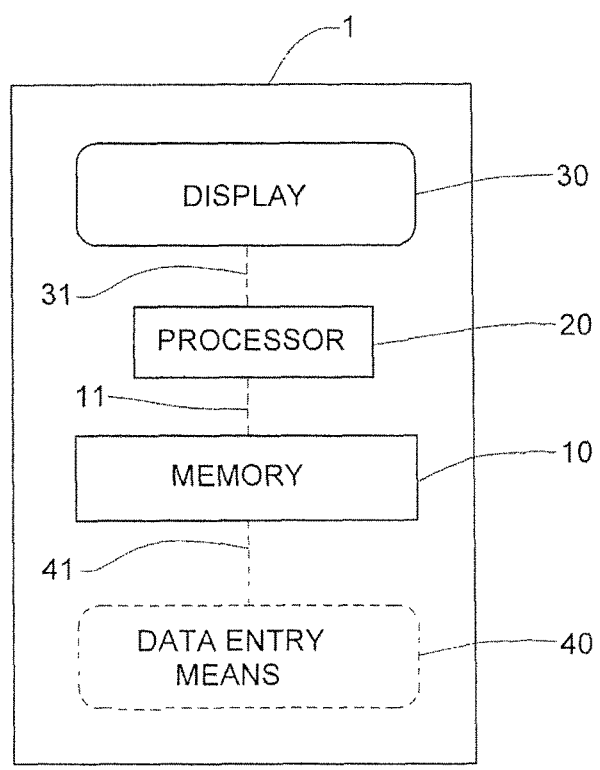
FIG. 1 is a simplified schematic of an apparatus according to a first exemplary embodiment of the invention.

Referring to FIG. 1, which constitutes a generalized schematic thereof, the inventive apparatus 1 according to an exemplary embodiment more particularly comprises at least a first memory 10 for storing data inputs corresponding at least to one or more components of a patient's present insulin dosage regimen (whether comprising separate units of long-acting and short-acting insulin, premixed insulin, etc.) and the patient's blood-glucose-level measurements determined at a plurality of times, a processor 20 operatively connected (indicated at line 11) to the at least first memory 10, and a display 30 operatively coupled (indicated at line 31) to the processor and operative to display at least information corresponding to the patient's present insulin dosage regimen. The processor 20 is programmed at least to determine from the data inputs corresponding to the patient's blood-glucose-level measurements determined at a plurality of times whether and by how much to vary at least one or the one or more components of the patient's present insulin dosage regimen in order to maintain the patient's future blood-glucose-level measurements within a predefined range. Such variation, if effected, leads to a modification of the patient's present insulin dosage regimen data as stored in the memory 10, as explained further herein. Thus, the data inputs corresponding to the one or more components of the patient's present insulin dosage regimen as stored in the memory device 10 will, at a starting time for employment of the inventive apparatus, constitute an insulin dosage regimen prescribed by a healthcare professional, but those data inputs may subsequently be varied by operation of the apparatus (such as during the time interval between a patient's clinic visits). In the foregoing manner, the inventive apparatus is operative to monitor relevant patient data with each new input of information (such as, at a minimum, the patient's blood-glucose-level measurements), thereby facilitating the optimization of the patient's insulin dosage regimen in between clinic visits.

It is contemplated that the apparatus as generalized above may be embodied in any of a variety of forms, including a purpose-built, PDA-like unit, a commercially available device such as a cell-phone, IPHONE, etc. Preferably, though not necessarily, such a device would include data entry means, such as a keypad, touch-screen interface, etc. (indicated generally at the dashed box 40) for the initial input by a healthcare professional of data corresponding at least to a patient's present insulin dosage regimen (and, optionally, such additional data inputs as, for instance, the patient's present weight, defined upper and lower preferred limits for the patient's blood-glucose-level measurements, etc.), as well as the subsequent data inputs corresponding at least to the patient's blood-glucose-level measurements determined at a plurality of times (and, optionally, such additional data inputs as, for instance, the patient's present weight, the number of insulin units administered by the patient, data corresponding to when the patient eats, the carbohydrate content of the foodstuffs eaten, the meal type (e.g., breakfast, lunch, dinner, snack, etc.). As shown, such data entry means 40 are operatively connected (indicated at line 41) to the memory 10.

Display 30 is operative to provide a visual display to the patient, healthcare professional, etc. of pertinent information, including, by way of non-limiting example, information corresponding to the present insulin dosage regimen for the patient, the current insulin dose (i.e., number of insulin units the patient needs to administer on the basis of the latest blood-glucose-level measurement and current insulin dosage regimen), etc. To that end, display 30 is operatively connected to the processor 20, as indicated by the dashed line 31.

As noted, the data entry means 40 may take the form of a touch-screen, in which case the data entry means 40 and display 30 may be combined (such as exemplified by the commercially available IPHONE (Apple, Inc., California)).

Referring then to FIGS. 2 through 5, there are depicted representative images for a display 30 and a touch-screen type, combined display 30/data entry means 40 exemplifying both the patient information that may be provided via the display, as well as the manner of data entry.

Figure 2:
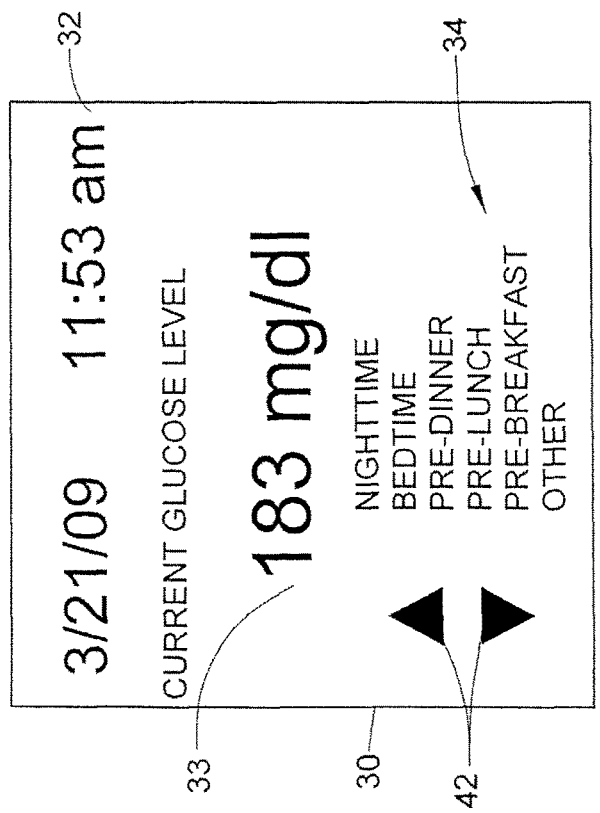
FIG. 2 is a drawing of a representative display for providing information to a patient.

More particularly, FIG. 2 shows a display 30 providing current date/time information 32 as well as the patient's current blood-glucose-level measurement 33 based upon a concurrent entry of that data. FIG. 2 further depicts a pair of scrolling arrows 42 by which the patient is able to scroll through a list 34 of predefined choices representing the time of the patient's said current blood-glucose-level measurement. As explained further herebelow in association with a description of an exemplary algorithm for implementing the invention, selection of one of these choices will permit the processor to associate the measurement data with the appropriate measurement time for more precise control of the patient's insulin dosage regimen.

Figure 3:
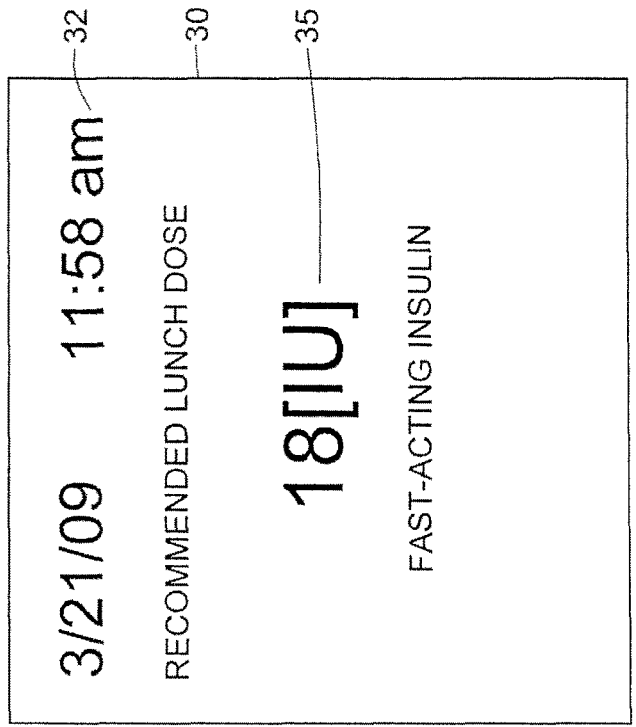
FIG. 3 is a drawing of another representative display for providing information to a patient.

FIG. 3 shows a display 30 providing current date/time information 32, as well as the presently recommended dose of short-acting insulin units 35—based upon the presently defined insulin dosage regimen—for the patient to take at lunchtime.

Figure 4:
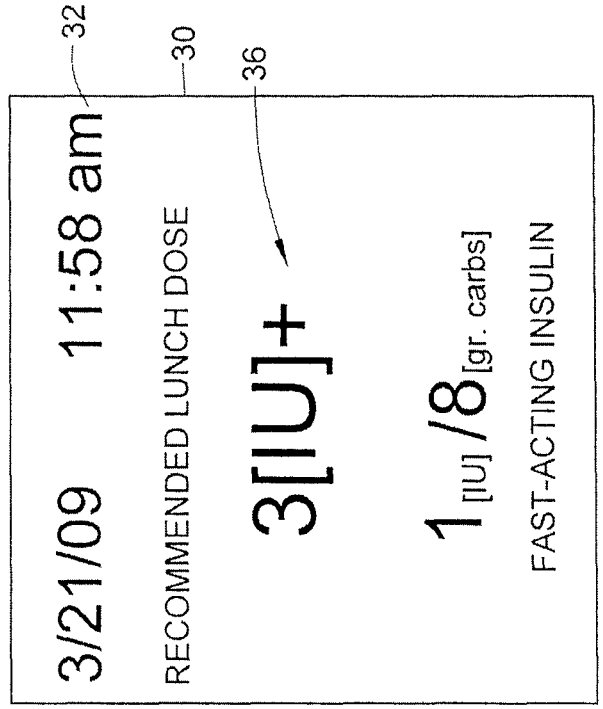
FIG. 4 is a drawing yet another representative display for providing information to a patient.

FIG. 4 shows a display 30 providing current date/time information 32, as well as, according to a conventional "carbohydrate-counting" therapy, the presently recommended base (3 IUs) and additional doses (1 IU per every 8 grams of carbohydrates ingested) of short-acting insulin units 36 for the patient to take at lunchtime—all based upon the presently defined insulin dosage regimen.

Figure 5:
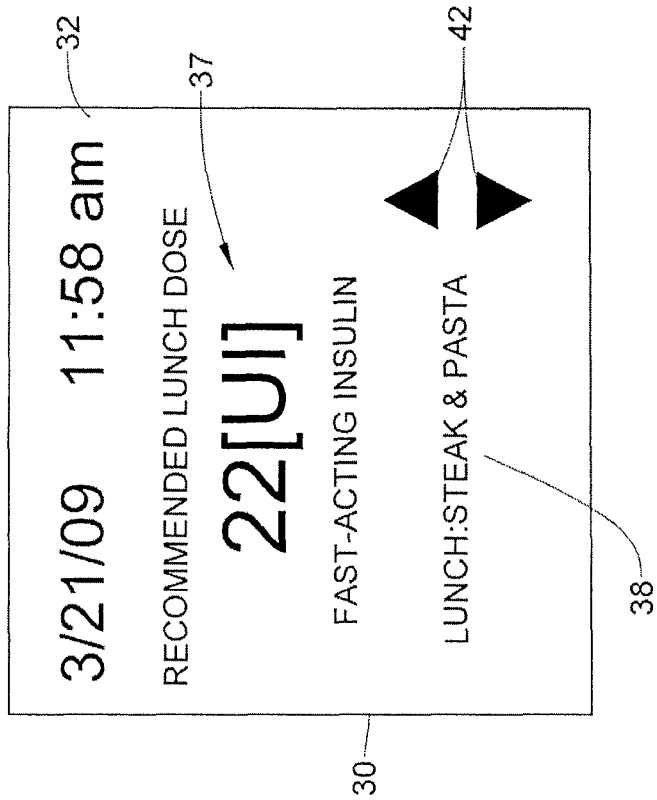
FIG. 5 is a drawing of still another representative display for providing information to a patient.

In FIG. 5, there is shown a display 30 providing current date/time information 32, as well as the presently recommended dose of short-acting insulin units 37—based upon the presently defined insulin dosage regimen—for the patient to take at lunchtime according to a designated amount of carbohydrates to be ingested. As further depicted in FIG. 5, a pair of scrolling arrows 42 are displayed, by which the patient is able to scroll through a list of predefined meal choices 38, each of which will have associated therewith in the memory a number (e.g., grams) of carbohydrates. When the patient selects a meal choice, the processor is able to determine from the number of carbohydrates associated with that meal, and the presently defined insulin dosage regimen, a recommended dose of short-acting insulin for the patient to take (in this example, 22 IUs of short-acting insulin for a lunch of steak and pasta).

Figure 6:
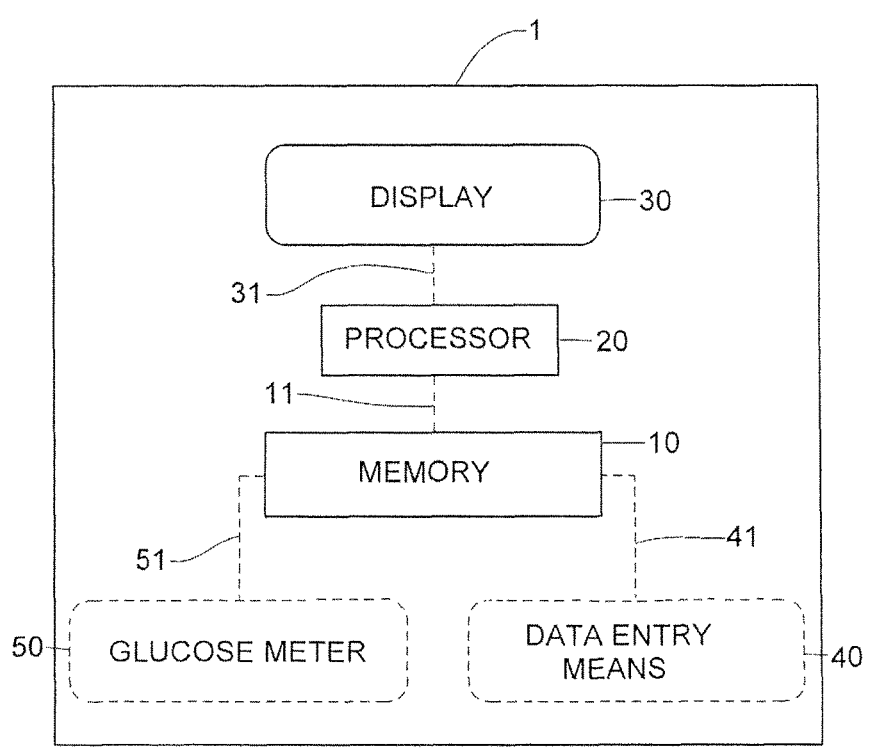
FIG. 6 is a simplified diagram of the an apparatus for employing the inventive system, according to a further embodiment thereof.

In one embodiment thereof, shown in FIG. 6, the inventive apparatus as described above in respect of FIG. 1 optionally includes a glucose meter (indicated by the dashed box 50) operatively connected (as indicated at line 51) to memory 10 to facilitate the automatic input of data corresponding to the patient's blood-glucose-level measurements directly to the memory 10.

Figure 7:
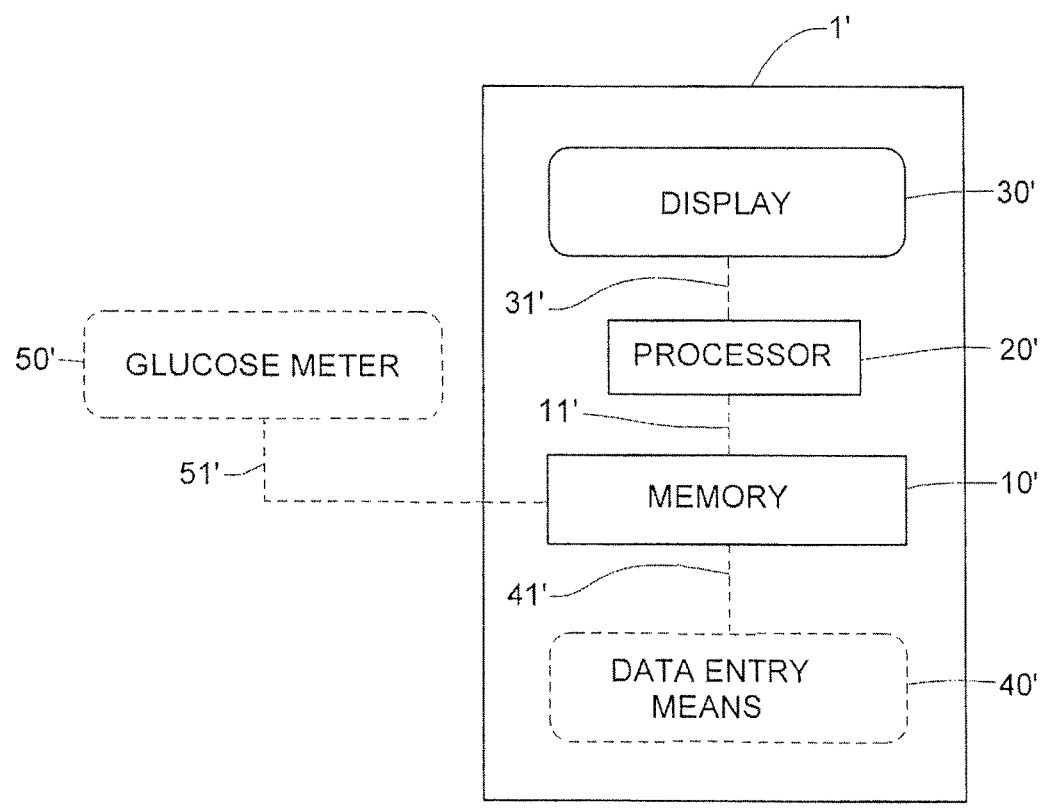
FIG. 7 is a simplified diagram of an apparatus for employing the inventive system, according to a further embodiment thereof.

Alternatively, it is contemplated that the glucose meter 50' could be provided as a separate unit that is capable of communicating (such as via a cable or wirelessly, represented at line 51') with the device 1' so as to download to the memory 10' the patient's blood-glucose-level measurements, such as shown in FIG. 7.

Figure 8:
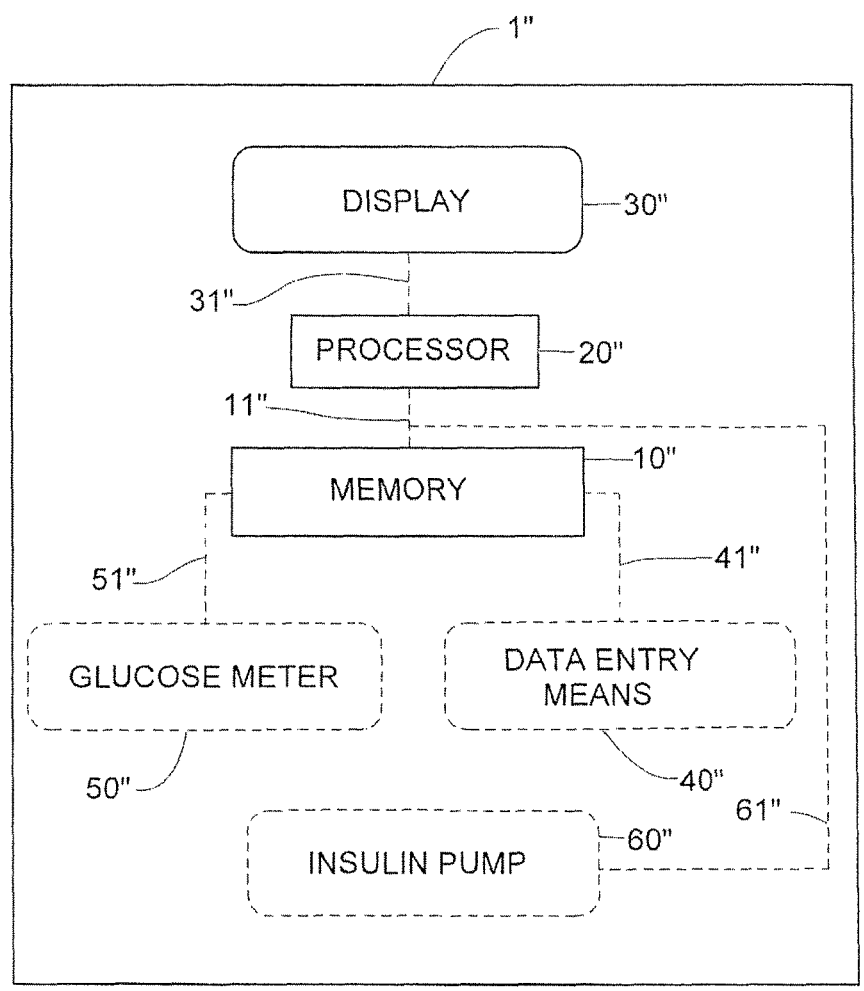
FIG. 8 is a simplified diagram of an apparatus for employing the inventive system, according to a further embodiment thereof.

According to another embodiment, shown in FIG. 8, the inventive apparatus 1" may be combined with an insulin pump 60" and, optionally, a glucose meter 50" as well. According to this embodiment, the processor 20" is operative to determine from at least the patient's blood-glucose-level measurement data (which may be automatically transferred to the memory 10" where the apparatus is provided with a glucose meter 50", as shown, is connectable to a glucose meter so that these data may be automatically downloaded to the memory 10", or is provided with data entry means 40" so that these data may be input by the patient) whether and by how much to vary the patient's present insulin dosage regimen in order to maintain the patient's future blood-glucose-level measurements within a predefined range. The processor 20", which is operatively connected to the insulin pump 60" (indicated at line 61"), is operative to employ the insulin dosage regimen information to control the insulin units provided to the patient via the pump 60". Therefore, the processor 20" and the pump 60" form a semi-automatic, closed-loop system operative to automatically adjust the pump's infusion rate and profile based on at least the patient's blood-glucose-level measurements. This will relieve the burden of having to go to the healthcare provider to adjust the insulin pump's infusion rate and profile, as is conventionally the case.

It will be appreciated that, further to this embodiment, the insulin pump 60" may be operative to transfer to the memory 10" data corresponding to the rate at which insulin is delivered to the patient by the pump according to the patient's present insulin dosage regimen. These data may be accessed by the processor 20" to calculate, for example, the amount of insulin units delivered by the pump to the patient over a predefined period of time (e.g., 24 hours). Such data may thus be employed in the present invention to more accurately determine a patient's insulin sensitivity, plasma glucose correction factor and carbohydrate ratio, for instance.

Also further to this embodiment, the apparatus 1" may optionally be provided with data entry means, such as a keypad, touch-screen interface, etc. (indicated generally at the dashed box 40") for entry of various data, including, for instance, the initial input by a healthcare professional of data corresponding at least to a patient's present insulin dosage regimen (and, optionally, such additional data inputs as, for instance, the patient's present weight, defined upper and lower preferred limits for the patient's blood-glucose-level measurements, etc.), as well as the subsequent data inputs corresponding at least to the patient's blood-glucose-level measurements determined at a plurality of times (to the extent that this information is not automatically transferred to the memory 10" from the blood glucose meter 50") and, optionally, such additional data inputs as, for instance, the patient's present weight, the number of insulin units administered by the patient, data corresponding to when the patient eats, the carbohydrate content of the foodstuffs eaten, the meal type (e.g., breakfast, lunch, dinner, snack), etc.

Figure 9:
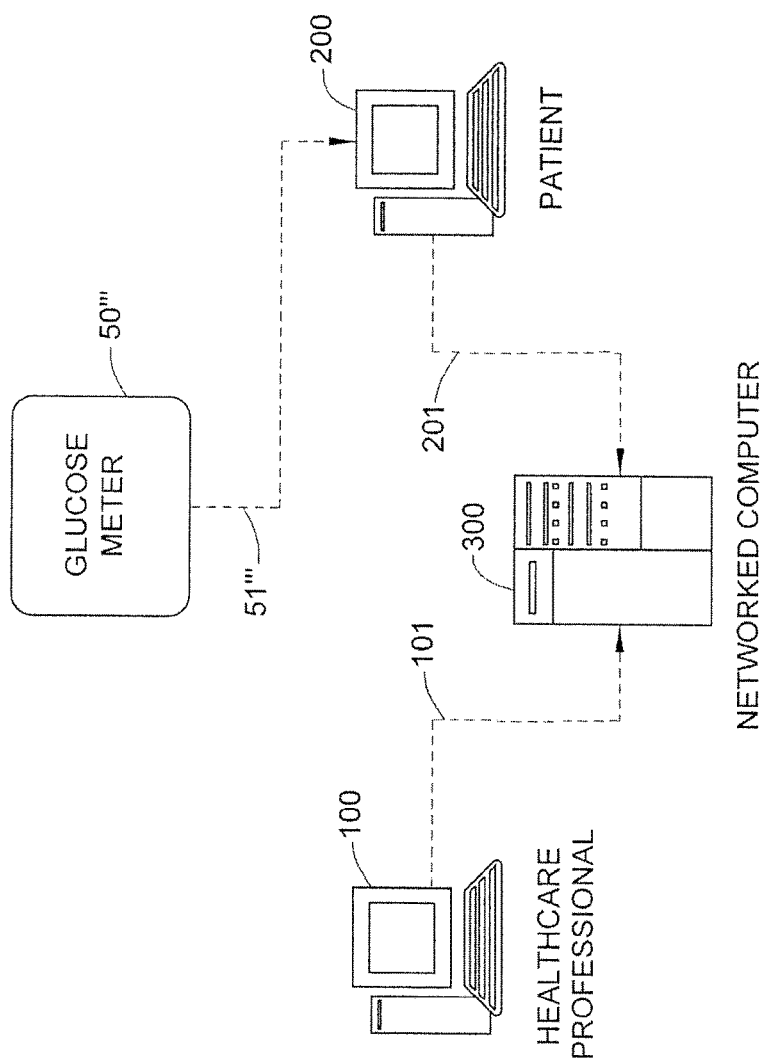
FIG. 9 is a schematic view of an exemplary arrangement for employing the present invention.

It is also contemplated that the invention may be effected through the input of data by persons (e.g., patient and healthcare professional) at disparate locations, such as illustrated in FIG. 9. For instance, it is contemplated that the data inputs pertaining to at least the patient's initial insulin dosage regimen may be entered by the healthcare professional at a first location, in the form of a general purpose computer, cell phone, IPHONE, or other device 100 (a general purpose computer is depicted), while the subsequent data inputs (e.g., patient blood-glucose-level readings) may be entered by the patient at a second location, also in the form of a general purpose computer, cell phone, IPHONE, or other device 200 (a general purpose computer is depicted), and these data communicated to a third location, in the form of a computer 300 comprising the at least first memory and the processor. According to this embodiment, the computers 100, 200, 300 may be networked in any known manner (including, for instance, via the Internet). Such networking is shown diagrammatically via lines 101 and 201. Thus, for instance, the invention may be implemented via a healthcare professional/patient accessible website through which relevant data are input and information respecting any updates to the predefined treatment plan are communicated to the patient and healthcare professional.

Figure 10:
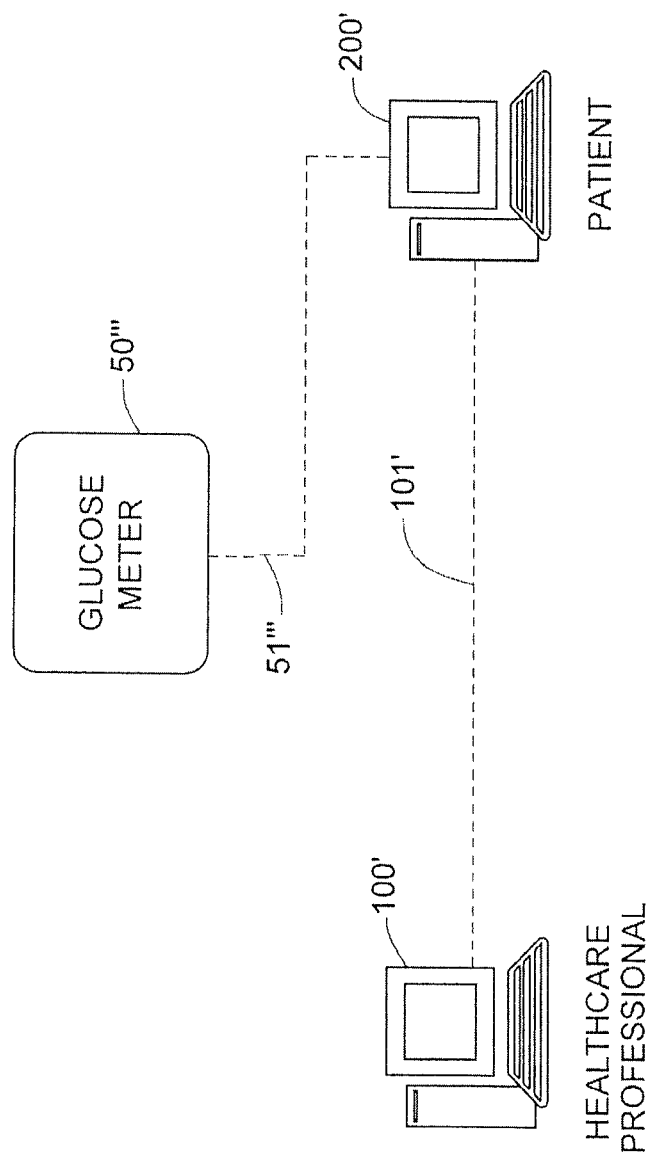
FIG. 10 is a schematic view of a second exemplary arrangement for employing the present invention.

Alternatively, it is contemplated that the invention may be effected through the input of data via persons (e.g., patient and healthcare professional) at disparate locations, and wherein further one of the persons, such as, in the illustrated example, the patient, is in possession of a single device 200' comprising the processor and memory components, that device 200' being adapted to receive data inputs from a person at a disparate location. FIG. 10. This device 200' could take any form, including a general-purpose computer (such as illustrated), a PDA, cell-phone, purpose-built device such as heretofore described, etc. According to this embodiment, it is contemplated that the data inputs pertaining to at least the patient's initial insulin dosage may be entered (for instance by the healthcare professional) at another location, such as via a general purpose computer, cell phone, or other device 100' (a general purpose computer is depicted) operative to transmit data to the device 200', while the subsequent data inputs (e.g., patient blood-glucose-level measurements) may be entered directly into the device 200'. According to this embodiment, a healthcare professional could remotely input the patient's initial insulin dosage at a first location via the device 100', and that data could then be transmitted to the patient's device 200' where it would be received and stored in the memory thereof. According to a further permutation of this embodiment, the aforedescribed arrangement could also be reversed, such that the patient data inputs (e.g., patient blood-glucose-level measurements) may be entered remotely, such as via a cell phone, computer, etc., at a first location and then transmitted to a remotely situated device comprising the processor and memory components operative to determine whether and by how much to vary the patient's present insulin dosage regimen. According to this further permutation, modifications to the patient's insulin dosage effected by operation of the invention could be transmitted back to the patient via the same, or alternate, means.

Referring again to FIG. 9, it is further contemplated that there may be provided a glucose meter 50''' (including, for instance, in the form of the device as described above in reference to FIG. 6) that can interface 51''' (wirelessly, via a hard-wire connection such as a USB cable, FIREWIRE cable, etc.) with a general purpose computer 200 at the patient's location to download blood-glucose-level measurements for transmission to the computer 300 at the third location. Referring also to FIG. 10, it is further contemplated that this glucose meter 50''' may be adapted to interface 51''' (wirelessly, via a hard-wire connection such as a USB cable, FIREWIRE cable, etc.) with the single device 200', thereby downloading blood-glucose-level measurement data to that device directly.

Figure 11:
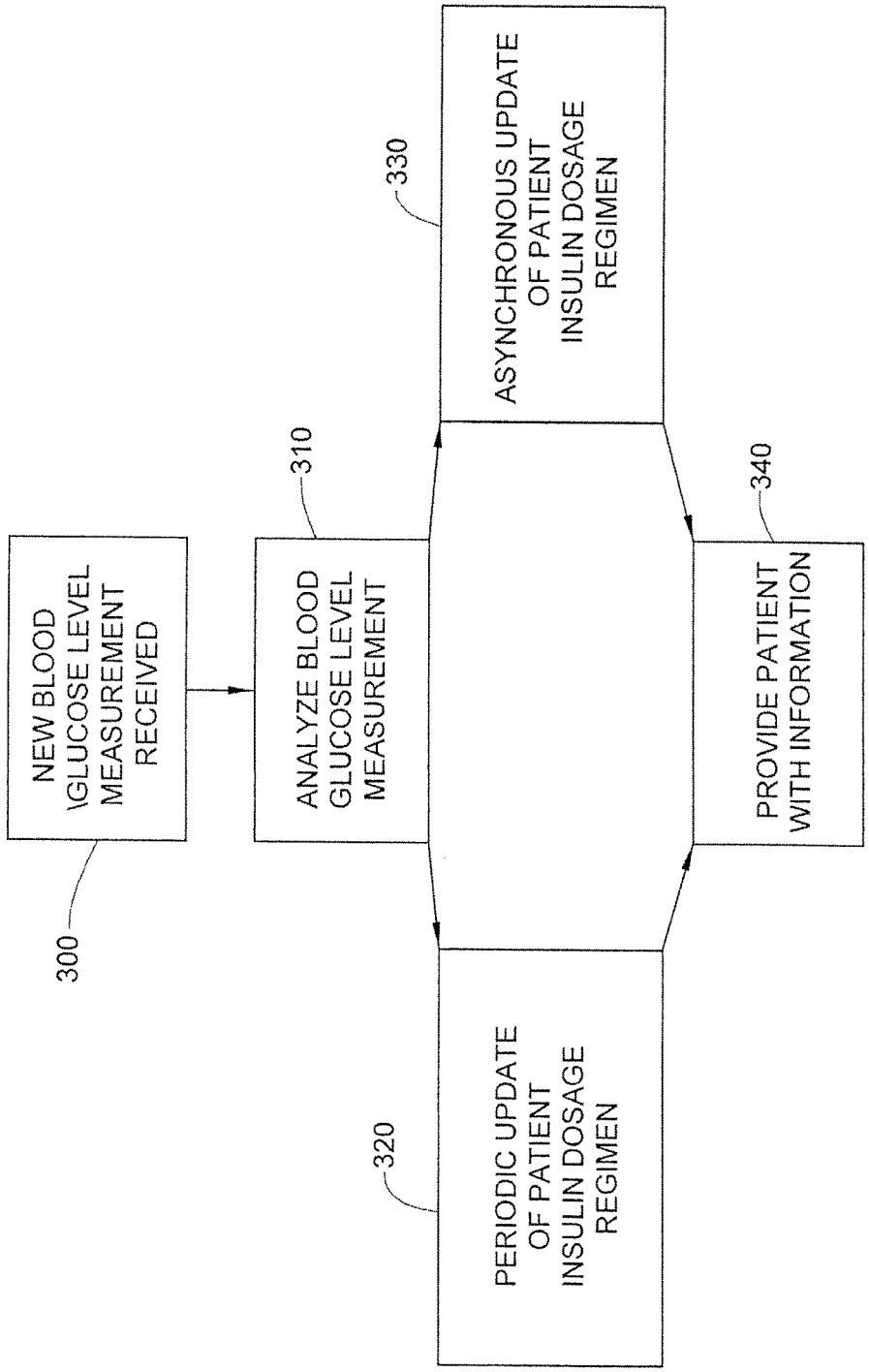
FIG. 11 is a generalized diagram of the steps employed in updating a patient's insulin dosage regimen according to an exemplary embodiment.

Turning now to FIG. 11, there is shown a diagram generalizing the manner in which the invention may be implemented to optimize a diabetes patient's insulin dosage regimen.

It will be understood that, in operation of the invention according to any of the several embodiments as described herein, there is initially specified, such as by a healthcare professional, a patient insulin dosage regimen (comprised of, for instance, a carbohydrate ratio ("CHR"), a long-acting insulin dose, and a plasma glucose correction factor). Alternatively, the initial insulin dosage regimen can be specified using published protocols for the initiation of insulin therapy, such as, for example, the protocols published by the American Diabetes Association on Oct. 22, 2008. However specified, this insulin dosage regimen data is entered in the memory of an apparatus (including according to any of the several embodiment described above), such as by a healthcare professional, in the first instance and before the patient has made any use of the apparatus.

Thereafter, the patient will input, or there will otherwise automatically be input (such as by the glucose meter) into the memory at least data corresponding to each successive one of the patient's blood-glucose-level measurements. Upon the input of such data, the processor determines, such as via the algorithm described herein, whether and by how much to vary the patient's present insulin dosage regimen. Information corresponding to this present insulin dosage regimen is then provided to the patient so that he/she may adjust the amount of insulin they administer.

According to the exemplary embodiment, determination of whether and by how much to vary a patient's present insulin dosage regimen is undertaken both on the basis of evaluations conducted at predefined time intervals (every 7 days, for example) as well as asynchronously to such intervals. The asynchronous determinations will evaluate the patient's blood-glucose-level data for safety each time a new blood-glucose-level measurement is received to determine whether any urgent action, including any urgent variation to the patient's present insulin dosage, is necessary.

More particularly, each time a new patient blood-glucose-level measurement is received 300 into the memory it is accessed by the processor and sorted and tagged according to the time of day the measurement was received and whether or not it is associated with a certain event, e.g., pre-breakfast, bedtime, nighttime, etc. 310. Once so sorted and tagged, the new and/or previously recorded blood-glucose-level measurements are subjected to evaluation for the need to update on the basis of the passage of a predefined period of time 320 measured by a counter, as well as the need to update asynchronously for safety 330. For instance, a very low blood glucose measurement (e.g., below 50 mg/dL) representing a severe hypoglycemic event or the accumulation of several low measurements in the past few days may lead to an update in the patient's insulin dosage regimen according to the step 330, while an update to that regimen may otherwise be warranted according to the step 320 if a predefined period of time (e.g., 7 days) has elapsed since the patient's insulin dosage regimen was last updated. In either case, the patient will be provided with information 340 corresponding to the present insulin dosage regimen (whether or not it has been changed) to be used in administering his/her insulin.

Figure 12:
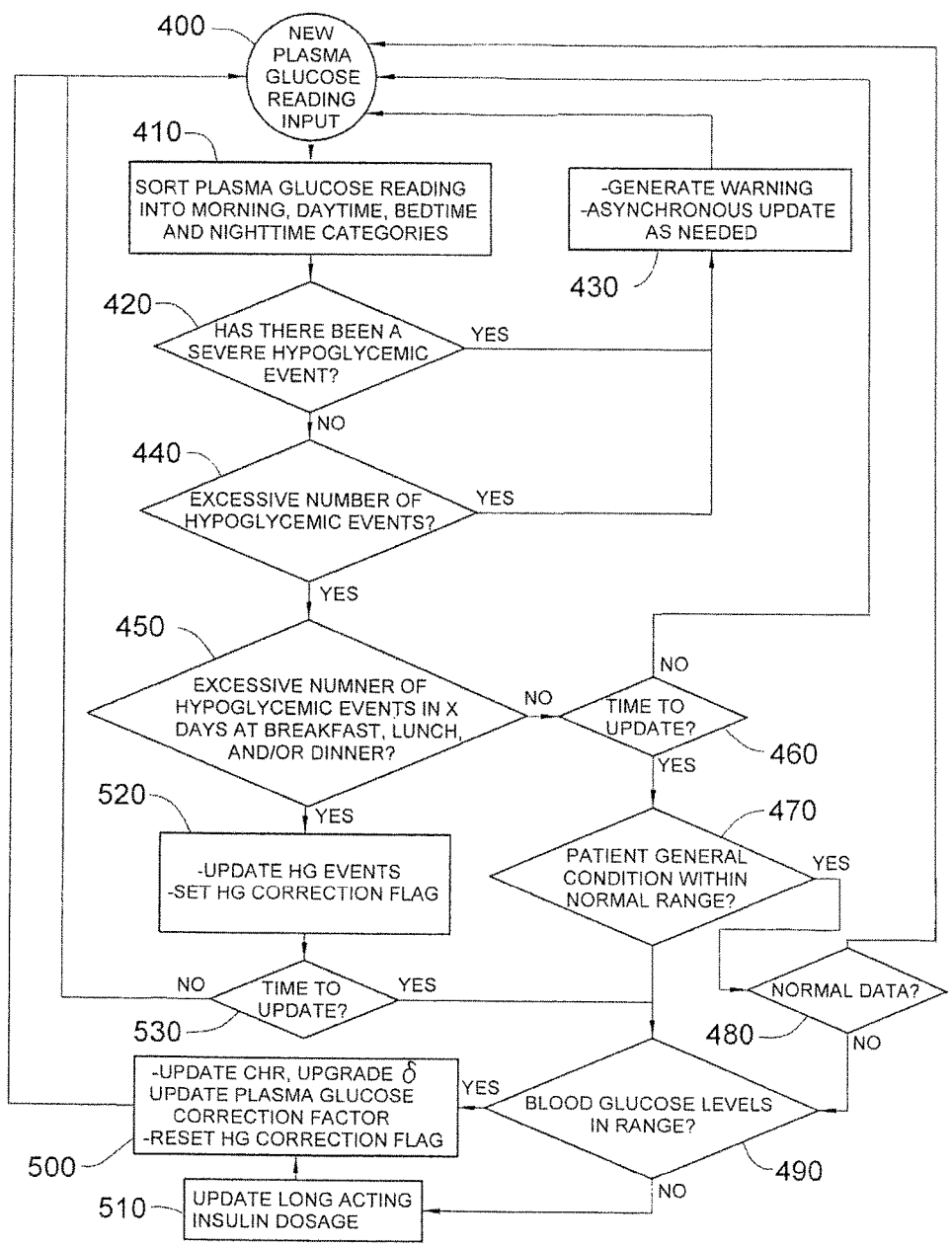
FIG. 12 is a flowchart of the exemplary algorithm employed in updating a patient's insulin dosage regimen according to an exemplary embodiment.

Referring next to FIG. 12, there is shown a flowchart that still more particularly sets forth an exemplary algorithm by which the invention may be implemented to optimize a diabetes patient's insulin dosage regimen. According to the exemplary algorithm, the insulin dosage modification contemplates separate units of long-acting and short-acting insulin. However, it will be appreciated that the invention is equally applicable to optimize the insulin dosage regimen of a patient where that dosage is in another conventional form (such as pre-mixed insulin). It will also be understood from this specification that the invention may be implemented otherwise than as particularly described hereinbelow.

According to a first step 400, data corresponding to a patient's new blood-glucose-level measurement is input, such as, for instance, by any of the exemplary means mentioned above, into the at least first memory (not shown in FIG. 12). This data is accessed and evaluated (by the processor) at step 410 of the exemplary algorithm and sorted according to the time it was input.

More particularly according to this step 410, the blood-glucose-level measurement data input is "tagged" with an identifier reflective of when the reading was input; specifically, whether it is a morning (i.e., "fast") measurement (herein "MPG"), a pre-lunch measurement (herein "BPG"), a pre-dinner measurement (herein "LPG"), a bedtime measurement (herein "BTPG"), or a nighttime measurement (herein "NPG").

The "tagging" process may be facilitated using a clock internal to the processor (such as, for instance, the clock of a general purpose computer) that provides an input time that can be associated with the blood-glucose-level measurement data synchronous to its entry. Alternatively, time data (i.e., "10:00 AM," "6:00 PM," etc.) or event-identifying information (i.e., "lunchtime," "dinnertime," "bedtime," etc.) may be input by the patient reflecting when the blood-glucose-level measurement data was taken, and such information used to tag the blood-glucose-level measurement data. As a further, alternative, and according to the embodiment where the blood-glucose-level measurement data are provided directly to the memory by a glucose monitor, time data may be automatically associated with the blood-glucose-level measurement data by such glucose monitor (for instance, by using a clock internal to that glucose monitor). It is also contemplated that, optionally, the user/patient may be queried (for instance at a display) for input to confirm or modify any time-tag automatically assigned a blood-glucose-level measurement data-input. Thus, for instance, a patient may be asked to confirm (via data entry means such as, for example, one or more buttons or keys, a touch-screen display, etc.) that the most recently input blood-glucose-level measurement data reflects a pre-lunch (BPG) measurement based on the time stamp associated with the input of the data. If the patient confirms, then the BPG designation would remain associated with the measurement. Otherwise, further queries of the patient may be made to determine the appropriate time designation to associate with the measurement.

It will be understood that any internal clock used to tag the blood-glucose-level measurement data may, as desired, be user adjustable so as to define the correct time for the time zone where the patient is located.

Further according to the exemplary embodiment, the various categories (e.g., DPG, MPG, LPG, etc.) into which the blood-glucose-level measurement data are more particularly sorted by the foregoing "tagging" process are as follows:

NPG—The data are assigned this designation when the time stamp is between 2 AM and 4 AM.

MPG—The data are assigned this designation when the time stamp is between 4 AM and 10 AM.

BPG—The data are assigned this designation when the time stamp is between 10 AM and 3 PM.

LPG—The data are assigned this designation when the time stamp is between 3 PM and 9 PM.

BTPG—The data are assigned this designation when the time stamp is between 9 PM and 2 AM. If the BTPG data reflect a time more than three hours after the patient's presumed dinnertime (according to a predefined time window), then these data are further categorized as a dinner compensation blood-glucose-level (herein "DPG").

According to the employment of a time stamp alone to "tag" the blood-glucose-level data inputs, it will be understood that there exists an underlying assumption that these data were in fact obtained by the patient within the time-stamp windows specified above.

Per the exemplary embodiment of the invention, if the time stamp of a blood-glucose-level measurement data-input is less than 3 hours from the measurement that preceded the last meal the patient had, it is considered biased and omitted unless it represents a hypoglycemic event.

According to the next step 420, the newly input blood-glucose-level measurement is accessed and evaluated (by the processor) to determine if the input reflects a present, severe hypoglycemic event. This evaluation may be characterized by the exemplary formula PG(t)<w, where PG(t) represents the patient's blood-glucose-level data in mg/dL, and w represents a predefined threshold value defining a severe hypoglycemic event (such as, by way of non-limiting example, 50 mg/dL).

If a severe hypoglycemic event is indicated at step 420 then, according to the step 430, the patient's present insulin dosage regimen data (in the memory 10 [not shown in FIG. 12]) is updated as warranted and independent of the periodic update evaluation described further below. More particularly, the algorithm will in this step 430 asynchronously (that is, independent of the periodic update evaluation) determine whether or not to update the patient's insulin dosage regimen on the basis of whether the patient's input blood-glucose-level data reflect the accumulation of several low glucose values over a short period of time. According to the exemplary embodiment, the dosage associated with the newly input blood-glucose-level measurement is immediately decreased. More specifically, for a severe hypoglycemic event at MPG, the long-acting insulin dosage is decreased by 20%; and for a severe hypoglycemic event at BPG the breakfast short-acting insulin dose is decreased by 20%.

The algorithm also at this step 430 updates a counter of hypoglycemic events to reflect the newly-input (at step 400) blood-glucose-level measurement. Notably, modifications to the patient's insulin dosage regimen according to this step 430 do not reset the timer counting to the next periodic update evaluation. Thus, variation in the patient's insulin dosage regimen according to this step 430 will not prevent the algorithm from undertaking the next periodic update evaluation.

Any such blood-glucose-level measurement is also entered into a hypoglycemic events database in the memory. In the exemplary embodiment, this is a rolling database that is not reset. Instead, the recorded hypoglycemic events expire from the database after a predefined period of time has elapsed; essentially, once these data become irrelevant to the patient's insulin dosage regime. Thus, by way of example only, this database may contain a record of a hypoglycemic event for 7 days.

Further according to the step 430, one or more warnings may be generated for display to the patient (such as via a display 30 [not shown in FIG. 12]). Most essentially, it is contemplated that such one or more warnings would alert a patient to the fact that his/her blood-glucose-level is dangerously low so that appropriate corrective steps (e.g., ingesting a glucose tablet) could be taken promptly. Additionally, and without limitation, such one or more warnings may also correspond to any one or more of the following determinations:

That the patient's blood-glucose-level measurement data reflect that there have been more than two hypoglycemic events during a predetermined period of time (such as, by way of example only, in the past 7 days); that more than two drops in the patient's blood-glucose-level measurements between the nighttime measurement and the morning measurement are greater than a predetermined amount in mg/dL (70 mg/dL, for instance); and/or that more than two drops in the patient's blood-glucose-level measurement between the nighttime measurement and the morning measurement are greater than a predetermined percentage (such as, for instance, 30%).

If a severe hypoglycemic event is not indicated at step 420, the recorded (in the memory 10) data inputs corresponding to the number of patient hypoglycemic events over a predetermined period of days are accessed and evaluated by the processor (20, not shown) at step 440 to determine if there have been an excessive number of regular hypoglycemic events (e.g., a blood-glucose-level measurement between 50 mg/dL and 75 mg/dL) over that predetermined period. This evaluation is essentially directed to determining whether the patient has experienced an excessive number of such regular hypoglycemic events in absolute time and independent of the periodic update operation as described elsewhere herein. This assessment, made at step 440, may be described by the following, exemplary formula:

Is (#{of events at HG}>Q) or is (#{of hypoglycemic events in the last W days}=Q)?

; where HG represents the recorded number of hypoglycemic events, W is a predefined period of time (e.g., 3 days), and Q is a predefined number defining an excessive number of hypoglycemic events (e.g., 3). By way of example, Q may equal 3 and W may also equal 3, in which case if it is determined in step 440 that there were either 4 recorded hypoglycemic events or there were 3 recorded hypoglycemic events in the last 3 days, the algorithm proceeds to step 430.

Notably, if step 440 leads to step 430, then a binary ("1" or "0") hypoglycemic event correction "flag" is set to "1," meaning that no increase in the patient's insulin dosage regimen is allowed and the algorithm jumps to step 490 (the periodic dosage update evaluation routine). Potentially, the periodic update evaluation may concur that any or all the parts of the insulin dosage regimen require an increase due to the nature of blood-glucose-levels currently stored in the memory 10 and the execution of the different formulas described hereafter. However, by setting the hypoglycemic event correction flag to "1," the algorithm will ignore any such required increase and would leave the suggested part of the dosage unchanged. Therefore, this will lead to a potential reduction in any or all the components of the insulin dosage regimen to thus address the occurrence of the excessive number of hypoglycemic events. Further according to this step, the timer counting to the next periodic update evaluation is reset.

In the next step 450, the recorded, time-sorted/tagged blood-glucose-level measurement data corresponding to the number of patient hypoglycemic events over a predetermined period of days (for example, 7 days) are accessed and evaluated by the processor to determine if there have been an excessive number of such hypoglycemic events at any one or more of breakfast, lunch, dinner and/or in the morning over the predetermined period. This evaluation may be characterized by the exemplary formula: #{HG(m)(b)(l)(d) in XX[d]}=Y?; where #HG(m)(b)(l)(d) represents the number of hypoglycemic events at any of the assigned (by the preceding step) measurement times of morning, bedtime, lunch or dinner over a period of XX (in the instant example, 7) days ("[d]"), and Y represents a number of hypoglycemic events that is predetermined to constitute a threshold sufficient to merit adjustment of the patient's insulin dosage regimen (in the present example, 2 hypoglycemic events). It will be appreciated that the employment of this step in the algorithm permits identification with greater specificity of possible deficiencies in the patient's present insulin dosage regimen. Moreover, the further particularization of when hypoglycemic events have occurred facilitates time-specific (e.g., after lunch, at bedtime, etc.) insulin dosage regimen modifications.

If an excessive number of such hypoglycemic events is not indicated at step 450, then the algorithm queries at step 460 whether or not it is time to update the patient's insulin dosage regimen irrespective of the non-occurrence of hypoglycemic events, and based instead upon the passage of a predefined interval of time (e.g., 7 days) since the need to update the patient's insulin dosage regimen was last assessed. If such an update is not indicated—i.e., because an insufficient time interval has passed—then no action is taken with respect to the patient's insulin dosage and the algorithm ends (indicated by the arrow labeled "NO") until the next blood-glucose-level measurement data are input.

If, however, an update is indicated by the fact that it has been 7 days (or other predefined interval) since the need to update the patient's insulin dosage was last evaluated, then before such update is effected the algorithm first determines, in step 470, if the patient's general condition falls within a predetermined "normal" range. This determination operation may be characterized by the exemplary formula: xxx≤E{PG}≥yyy; where xxx represents a lower bound for a desired blood-glucose-level range for the patient, yyy represents an upper bound for a desired blood-glucose-level range for the patient, and E{PG} represents the mean of the patient's recorded blood-glucose-level measurements. According to the exemplary embodiment, the lower bound xxx may be predefined as 80 mg/dL, and the upper bound yyy may be predefined as 135 mg/dL.

It will be understood that the foregoing values may be other than as so specified, being defined, for instance, according to the particular country in which the patient resides. Furthermore, it is contemplated that the upper (yyy) and lower (xxx) bounds may be defined by the patient's healthcare professional, being entered, for instance, via data entry means such as described elsewhere herein.

Where the patient's general condition is outside of the predetermined "normal" range, the algorithm proceeds to step 490 where the data are evaluated to determine whether it is necessary to correct the patient's long-acting insulin dosage regimen.

Where, however, the patient's general condition is within the predetermined "normal" range, the algorithm next (step 480) queries whether the patient's recorded blood-glucose-level measurement data represent a normal (e.g., Gaussian) or abnormal distribution. This may be characterized by the exemplary formula: —X<E{PG^3}<X; where E{PG^3} represents the third moment of the distribution of the recorded (in the memory) blood-glucose-level measurement data—i.e., the third root of the average of the cubed deviations in these data around the mean of the recorded blood-glucose-levels, and X represents a predefined limit (e.g., 5). It is contemplated that the predefined limit X should be reasonably close to 0, thus reflecting that the data (E{PG^3}) are well balanced around the mean.

Thus, for example, where X is 5, the data are considered to be normal when the third root of the average of the cubed deviations thereof around the mean of the recorded blood-glucose-levels is greater than −5 but less than 5. Otherwise, the data are considered to be abnormal.

Where the data are determined to be normal in step 480 (indicated by the arrow labeled "YES"), then no action is taken to update the patient's insulin dosage regimen.

However, if in step 470 the mean of all of a patient's recorded blood-glucose-level measurement data are determined to fall outside of the predetermined "normal" range, then in step 490 the algorithm evaluates whether it is necessary to correct the patient's long-acting insulin dosage regimen. This is done by evaluating whether the patient's recorded MPG and BTPG data fall within an acceptable range or, alternatively, if there is an indication that the patient's long-acting insulin dosage should be corrected due to low MPG blood-glucose-level measurements. The determination of whether the patient's MPG and BTPG data fall within a predetermined range may be characterized by the exemplary formula: xxy≤E{MPG}, E{BTPG}≤yyx; where xxy is a lower bound for a desired blood-glucose-level range for the patient, yyx is an upper bound for a desired blood-glucose-level range for the patient, E{MPG} represents the mean of the patient's recorded MPG blood-glucose-level measurements, and E{BTPG} represents the mean of the patient's recorded BTPG measurements. According to the exemplary embodiment, xxy may be predefined as 80 mg/dL, while yyx may be predefined as 200 mg/dL. However, it will be understood that these values may be otherwise predefined, including, as desired, by the patient's healthcare provider (being entered into the memory via data entry means, for instance).

If the determination in step 490 is positive, then update of the patient's long-acting insulin dosage (step 510) is bypassed and the algorithm proceeds to step 500, according to which the patient's short-acting insulin dosage (in the form of the carbohydrate ratio ("CHR"), a correction factor δ, and the plasma glucose correction factor are each updated and the hypoglycemic correction "flag" reset to 0 (thus permitting subsequent modification of the insulin dosage regimen at the next evaluation thereof).

If, on the other hand, the determination in step 490 is negative, then the patient's long-acting insulin dosage is updated at step 510, along with performance of the updates specified at step 500. In either case, the process ends following such updates until new patient blood-glucose-level measurement data are input.

Updates of the long-acting insulin dosage regimen data may be characterized by the following, exemplary formulas:

$$\Delta_{up} = (1 - \alpha(2))\text{floor}\left\{\frac{\alpha(1)LD(k)}{100}\right\} + \alpha(2)\text{ceil}\left\{\frac{\alpha(1)LD(k)}{100}\right\}$$

$$\Delta_{down} = (1 - \alpha(2))\text{floor}\left\{\frac{\alpha(1)LD(k)}{200}\right\} + \alpha(2)\text{ceil}\left\{\frac{\alpha(1)LD(k)}{200}\right\}$$

-continued

If $E\{MPG\} < b_1$ $LD(k + 1) = LD(k) - \Delta_{down}$

Else

If $E\{MPG\} > b_2$ $LD(k + 1) = LD(k) + \Delta_{up}$

Else if $E\{MPG\} > b_3$ $LD(k + 1) = LD(k) + \Delta_{down}$

End

End;

where $\alpha(1)$ represents a percentage by which the patient's present long-acting insulin dosage regimen is to be varied, $\alpha(2)$ represents a corresponding binary value (due to the need to quantize the dosage), LD(k) represents the patient's present dosage of long-acting insulin, LD(k+1) represents the new long-acting insulin dosage, $b_1$, $b_2$, and $b_3$ represent predetermined blood-glucose-level threshold parameters in mg/dL, and E{MPG} is the mean of the patient's recorded MPG blood-glucose-level measurements.

Since a patient's insulin dosage regimen is expressed in integers (i.e., units of insulin), it is necessary to decide if a percent change (increase or decrease) in the present dosage regimen of long-acting insulin that does not equate to an integer value should be the nearest higher or lower integer. Thus, for instance, if it is necessary to increase by 20% a patient's long-acting insulin dosage regimen from a present regimen of 18 units, it is necessary to decide if the new dosage should be 21 units or 22 units. In the exemplary algorithm, this decision is made on the basis of the patient's insulin sensitivity.

Insulin sensitivity is generally defined as the average total number of insulin units a patient administer per day divided by the patient weight in kilograms. More particularly, insulin sensitivity (IS(k)) according to the exemplary algorithm may be defined as a function of twice the patient's total daily dosage of long-acting insulin (which may be derived from the recorded data corresponding to the patient's present insulin dosage regimen) divided by the patient's weight in kilograms. This is expressed in the following exemplary formula:

$$IS(k) = \frac{2 \cdot LD(k)}{KK};$$

where KK is the patient weight in kilograms.

A patient's insulin sensitivity factor may of course be approximated by other conventional means, including without reliance on entry of data corresponding to the patient's weight.

More particularly, the inventive algorithm employs an insulin sensitivity correction factor ($\alpha_{(2\times1)}(IS))$), a 2 entries vector, to determine the percentage at which the dosage will be corrected and to effect an appropriate rounding to the closest whole number for updates in the patient's CHR, PGR and LD. When the patient's weight is known, this determination may be characterized by the following, exemplary formula:

$$\alpha(IS) = \begin{cases} [5\ 0]', & IS(k) < y_1 \\ [10\ 0]', & y_1 \leq IS(k) < y_2 \\ [20\ 0]', & y_2 \leq IS(k) < y_3 \\ [20\ 1]', & y_3 \leq IS(k); \end{cases}$$

where $\alpha(1)$ is a percentage value of adjustment from the present to a new insulin dosage value, and $\alpha(2)$ is a binary value (i.e., 0 or 1). The value of $\alpha(2)$ is defined by the value of IS(k) in relation to a predefined percent change value (e.g., $y_1$, $y_2$, $y_3$, $y_4$) for $\alpha(1)$. Thus, in the exemplary embodiment of the algorithm: Where, for example, IS(k) <0.3, the value of $\alpha(1)$ is 5 and the value of $\alpha(2)$ is 0; where $0.3 \leq IS(k) < 0.5$, the value of $\alpha(1)$ is 10 and the value of $\alpha(2)$ is 0; where $0.5 \leq IS(k) < 0.7$, the value of $\alpha(1)$ is 20 and the value of $\alpha(2)$ is 0; and where $0.7 \leq IS(k)$, the value of $\alpha(1)$ is 20 and the value of $\alpha(2)$ is 1.

When the patient weight is unknown, the algorithm will determine a using the following alternative: $\alpha(2)$ is set to "1" if the patient long acting insulin dosage is greater than X units (where, for example X may equal 50 insulin units), and the percentage by which we adjust the dosage will be determined according to the mean of all blood-glucose-level measurements currently in memory (i.e., E{PG}) by:

$$\alpha(1) = \begin{cases} 5, & w_1 \leq E\{PG\} < w_2 \\ 10, & w_2 \leq E\{PG\} < w_3 \\ 20, & w_3 \leq E\{PG\}; \end{cases}$$

where $w_1$, $w_2$ and $w_3$ each represent a predefined blood-glucose-level expressed in mg/dL (thus, for example, $w_1$ may equal 135 mg/dL, $w_2$ may equal 200 mg/dL, and $w_3$ may equal 280 mg/dL).

Returning to the exemplary formulas for updating the patient's long-acting insulin dosage, in the exemplary algorithm the decision of whether and by how much to decrease or increase a patient's long-acting insulin dosage regimen is based on the predetermined threshold parameters $b_1$, $b_2$, and $b_3$; where, by way of example only, $b_1$=80 mg/dL, $b_2$=120 mg/dL, and $1)_3$=200 mg/dL. More particularly, where the mean of the patient's MPG blood-glucose-level data is less than 80 mg/dL, the new long-acting insulin dosage (LD(k+1)) is the present long-acting insulin dosage (LD(k)) minus the value of $\Delta_{down}$ (which, as shown above, is a function of the insulin sensitivity correction factors $\alpha(1)$ and $\alpha(2)$, and the patient's long-acting insulin dosage (LD(k)) and may equal half of $\Delta_{up}$). Otherwise, if the mean of the patient's MPG blood-glucose-level data is greater than 200 mg/dL, the new long-acting insulin dosage (LD(k+1)) is the present long-acting insulin dosage (LD(k)) plus the value of the $\Delta_{up}$ (which, as shown above, is a function of the insulin sensitivity correction factors $\alpha(1)$ and $\alpha(2)$, and the patient's long-acting insulin dosage (LD(k)). Finally, if the mean of the patient's MPG blood-glucose-level data is greater than 150 but less than 200, the new long-acting insulin dosage (LD(k+1)) is the present long-acting insulin dosage (LD(k)) plus the value of the $\Delta_{down}$.

The corrective amount $\Delta$ is calculated as a percentage of the current long-acting insulin dosage rounded according to $\alpha(2)$. In a particular example, if $\alpha(1)$=20, $\alpha(2)$=0, and the current long acting insulin dosage LD(k)=58, then $\Delta_{up}$ equals 20% of 58, which is 11.6, rounded down to $\Delta_{up}$=11.

Accordingly, the long-acting insulin dosage would be updated to LD(k+1)=58+11=69.

It will be appreciated by reference to the foregoing that no "ping-pong" effect is allowed; in other words, the patient's long-acting insulin dosage may not be adjustable so that any two successive such adjusted dosages fall below and above the dosage which they immediately succeed. Thus, it is not permitted to have the outcome where the latest LD update (LD(2)) is greater than the initial LD set by the healthcare professional (LD(0)), and the preceding LD update (LD(1)) is less than LD(0). Thus, the outcome LD(2)>LD(0)>LD(1) is not permitted.

Returning to the step 450, if an excessive number of hypoglycemic events at any of the time-tagged blood-glucose-level measurement data for breakfast, lunch, dinner or in the morning over the predetermined period (for instance, 7 days) are indicated from the patient's data, then at step 520 the algorithm identifies from the recorded, time-tagged data of hypoglycemic events when those events occurred in order to affect any subsequently undertaken variation to the patient's insulin dosage regimen, and also sets the binary hypoglycemic correction "flag" (e.g., "1" or "0", where 1 represents the occurrence of too many hypoglycemic events, and 0 represents the nonoccurrence of too many hypoglycemic events) to 1. The presence of this "flag" in the algorithm at this juncture prevents subsequent increases in the patient's insulin dosage regimen in the presence of too many hypoglycemic events.

Further according to this step 520, where the blood-glucose-level measurement data reflects hypoglycemic events in the morning or during the night, the algorithm identifies the appropriate modification required to any subsequent variation of the patient's insulin dosage regimen. This may be characterized by the following, exemplary formula: If #HG events in {MPG+NTPG}=X, then reduce LD by $\alpha(1)/2$; where #HG is the number of recorded patient hypoglycemic events at the MPG and NTPG-designated blood-glucose-level measurements, X is a predefined value (such as, for example, 2), LD refers to the long-acting insulin dosage, and $\alpha(1)$ represents the aforedescribed insulin sensitivity correction factor, expressed as a percentage. Thus, $\alpha(1)/2$ reflects that the patient's long-acting insulin dosage is to be reduced only by ½ of the value of $\alpha(1)$, if at all, where the recorded hypoglycemic events occur in the morning or overnight.

Further according to this step 520, where the blood-glucose-level measurement data reflects hypoglycemic events during the day, the algorithm identifies the appropriate modification required to any subsequent variation of the patient's insulin dosage regimen. This may be characterized by the following formula: If #HG events in {BPG or LPG or NTPG}=X, then see update $\delta$; where #HG is the number of recorded patient hypoglycemic events at any of the BPG, LPG or NTPG time-tagged measurements, X is a predefined value (for instance, 2), and "see update $\delta$" refers to short-acting insulin dosage correction factor $\delta$ incorporated into the exemplary form of the algorithm, as described herein.

Following step 520, the algorithm queries 530 whether it is time to update the patient's insulin dosage regimen irrespective of the occurrence of hypoglycemic events and based upon the passage of a predefined interval of time (by way of non-limiting example, 7 days) since the need to update the patient's insulin dosage regimen was last assessed. Thus, it is possible that a patient's insulin dosage regimen will not be updated even though the HG correction flag has been "tripped" (indicating the occurrence of too many hypoglycemic events) if an insufficient period of time has passed since the regimen was last updated.

If an insufficient period of time has passed, the process is at an end (indicated by the arrow labeled "NO") until new blood-glucose-level measurement data are input. If, on the other hand, the predefined period of time has passed, then the algorithm proceeds to the step 490 to determine if the long-acting insulin dosage has to be updated as described before followed by the update step 500, according to which the patient's short-acting insulin dosage (in the form of the carbohydrate ratio ("CHR")), the correction factor $\delta$, and plasma glucose correction factor are each updated and the hypoglycemic correction flag reset to 0.

According to the step 500, an update to the patient's plasma glucose correction factor ("PGR") is undertaken. This may be characterized by the following, exemplary formulas:

$$\text{Calculate new } PGR(\text{"}NPGR\text{"}): NPGR = \frac{1700}{E\{DT\}}.$$

Calculate difference, $\Delta = |PGR(k) - NPGR|$

If $$\frac{\Delta}{PGR(k)} \leq \frac{\alpha(1)}{100}$$

$\Delta = (1 - \alpha(2))\text{floor}\{\Delta\} + \alpha(2)\text{ceil}\{\Delta\}$ Else $$\Delta = (1 - \alpha(2))\text{floor}\left\{\frac{\alpha(1)PGR(k)}{100}\right\} + \alpha(2)\text{ceil}\left\{\frac{\alpha(1)PGR(k)}{100}\right\}$$

End $PGR(k + 1) = PGR(k) + \Delta \cdot \text{sign}(NPGR - PGR(k))$ $PGR(k + 1) = \text{quant}(PGR(k + 1), ZZ);$ Quantize correction to steps of ZZ[mg/dL].

More particularly, the new PGR ("NPGR") is a function of a predefined value (e.g., 1700) divided by twice the patient's total daily dosage of long-acting insulin in the present insulin dosage regimen. In the foregoing formulas, the value of this divisor is represented by $E\{DT\}$, since the value representing twice the patient's daily dosage of long-acting insulin in the present insulin dosage regimen is substituted as an approximation for the mean of the total daily dosage of insulin administered to the patient (which data may, optionally, be employed if they are input into the memory by an insulin pump, such as in the exemplary apparatus described above, or by the patient using data entry means). The resultant value is subtracted from the present patient PGR ("PGR(k)") to define a difference ("$\Delta$"). If the $\Delta$ divided by the present PGR(k) is less than or equal to the value of $\alpha(1)$ divided by 100, then the integer value of $\Delta$ (by which new PGR (i.e., PGR(k+1)) is updated) is a function of the formula $\Delta=(1-\alpha(2))\text{floor}\{\Delta\}+\alpha(2)\text{ceil}\{\Delta\}$, where $\alpha(2)$ is the insulin sensitivity correction factor (1 or 0), "floor" is value of $\Delta$ rounded down to the next integer, and "ceil" is the value of $\Delta$ rounded up to the next integer. If, on the other hand, the $\Delta$ divided by the present PGR(k) is greater than the value of $\alpha(1)$ divided by 100, then the integer value of $\Delta$ is a function of the formula $$\Delta = (1 - \alpha(2))\text{floor}\left\{\frac{\alpha(1)PGR(k)}{100}\right\} + \alpha(2)\text{ceil}\left\{\frac{\alpha(1)PGR(k)}{100}\right\},$$

where α(2) is the insulin sensitivity correction factor (1 or 0), α(1) is the percent value of the insulin sensitivity correction factor, PGR(k) is the present PGR, "floor" is value of Δ rounded down to the next integer, and "ceil" is the value of Δ rounded up to the next integer. According to either outcome, the new PGR (PGR(k+1)) is equal to the present PGR (PGR(k)) plus Δ times the sign of the difference, positive or negative, of NPGR minus PGR(k).

Furthermore, it is contemplated that the new PGR will be quantized to predefined steps of mg/dL. This is represented by the exemplary formula: PGR(k+1)=quant(PGR(k+1), ZZ)PGR(k+1)=quant(PGR(k+1), ZZ); where, by way of a non-limiting example, ZZ may equal 5.

Also according to the update step 500, updates to the patient's short-acting insulin dosage regimen are undertaken by modifying the carbohydrate ratio (CHR). CHR represents the average carbohydrate to insulin ratio that a patient needs to determine the correct dose of insulin to inject before each meal. This process may be characterized by the following, exemplary formulas:

Calculate new $CHR("NCHR")$, $NCHR = \dfrac{500}{E\{DT\}}$

Calculate difference, $\Delta = |CHR(k) - NCHR|$

If $\dfrac{\Delta}{CHR(k)} \leq \dfrac{\alpha(1)}{100}$ $\Delta = (1 - \alpha(2))\text{floor}\{\Delta\} + \alpha(2)\text{ceil}\{\Delta\}$ Else $\Delta = (1 - \alpha(2))\text{floor}\left\{\dfrac{\alpha(1)CHR(k)}{100}\right\} + \alpha(2)\text{ceil}\left\{\dfrac{\alpha(1)CHR(k)}{100}\right\}$ End $CHR(k+1) = CHR(k) + \Delta \cdot \text{sign}(NCHR - CHR(k))$ More particularly, the new CHR ("NCHR") is a function of a predefined value (e.g., 500) divided by twice the patient's total daily dosage of long-acting insulin in the present insulin dosage regimen. In the foregoing formulas, the value of this divisor is represented by E{DT}, since the value representing twice the patient's daily dosage of long-acting insulin in the present insulin dosage regimen is substituted as an approximation for the mean of the total daily dosage of insulin administered to the patient (which data may, optionally, be employed if they are input into the memory by an insulin pump, such as in the exemplary apparatus described above, or by the patient using data entry means). The resultant value is subtracted from the present patient CHR ("CHR(k)") to define a difference ("Δ"). If the Δ divided by the present CHR(k) is less than or equal to the value of α(1) divided by 100, then the integer value of Δ (by which new CHR (i.e., CHR(k+1)) is updated) is a function of the formula Δ=(1−α(2))floor{Δ}+α(2)ceil{Δ}, where α(2) is the insulin sensitivity correction factor (1 or 0), "floor" is value of Δ rounded down to the next integer, and "ceil" is the value of Δ rounded up to the next integer. If, on the other hand, the Δ divided by the present CHR(k) is greater than the value of α(1) divided by 100, then the integer value of Δ is a function of the formula $\Delta = (1 - \alpha(2))\text{floor}\left\{\dfrac{\alpha(1)CHR(k)}{100}\right\} + \alpha(2)\text{ceil}\left\{\dfrac{\alpha(1)CHR(k)}{100}\right\}$, where α(2) is the insulin sensitivity correction factor (1 or 0), α(1) is the percent value of the insulin sensitivity correction factor, CHR(k) is the present CHR, "floor" is value of Δ rounded down to the next integer, and "ceil" is the value of Δ rounded up to the next integer. According to either outcome, the new CHR (CHR(k+1)) is equal to the present CHR (CHR(k)) plus Δ times the sign of the difference, positive or negative, of NCHR minus CHR(k).

As patients may respond differently to doses of short-acting insulin depending upon the time of day the injection is made, a different dose of insulin may be required to compensate for a similar amount of carbohydrates consumed for breakfast, lunch, or dinner. For example, one may administer '1' insulin unit for every '10' grams of carbohydrates consumed at lunch while administering '1' insulin unit for every '8' grams of carbohydrates consumed at dinner. In the exemplary embodiment of the algorithm, this flexibility is achieved by the parameter Delta, δ, which is also updated in the step 500. It will be understood that the carbohydrate to insulin ratio (CHR) as calculated above is the same for all meals. However, the actual dosage differs among meals (i.e., breakfast, lunch, dinner) and equals CHR-δ. Therefore, the exemplary algorithm allows the dosage to be made more effective by slightly altering the CHR with δ to compensate for a patient's individual response to insulin at different times of the day.

Delta δ is a set of integers representing grams of carbohydrates, and is more specifically defined as the set of values [δb, δl, δd], where "b" represents breakfast, "l" represents lunch, and "d" represents dinner. Delta, δ, may be either positive—thus reflecting that before a certain meal it is desired to increase the insulin dose—or negative—thus reflecting that due to hypoglycemic events during the day it is desired to decrease the insulin dose for a given meal.

Initially, it is contemplated that each δ in the set [δb, δl, δd] may be defined by the patient's healthcare professional or constitute a predefined value (e.g., δ=[0, 0, 0] for each of [b, l, d], or [0b, 0l, 0d], thus reflecting that the patient's CHR is used with no alteration for breakfast, lunch, or dinner).

The range of δ ("Rδ") is defined as the maximum of three differences, expressed as max(|δb−δl|, |δb−δd|, |δd−δl|). In addition the algorithm defines the minimal entry ("$\delta_{min}$") of the set [δb, δl, δd], expressed as min(δb, δl, δd).

Any correction to the patient's CHR can only result in a new Rδ ("Rδ(k+1)") that is less than or equal to the greatest of the range of the present set of δ(Rδ(k)) or a predefined limit (D), which may, for instance, be 2, as in the exemplary embodiment.

Against the foregoing, if the number of hypoglycemic events (HG) in a given meal (b, l or d) over a predefined period (for example, 7 days) is equal to a predefined value (for instance, 2), and if the corresponding δb, δl, or δd is not equal to the $\delta_{min}$ or the range is 0 ($R_\delta=0$), then the decrease in that δ (δb, δl, or δd) is equal to the present value for that δ minus a predefined value ("d"), which may, for instance, be 1; thus, $\delta_{\{i\}} = \delta_{\{i\}} - d$.

Otherwise, if the corresponding δb, δl, or δd is equal to the $\delta_{min}$ and the range is other than 0, then the decrease in that δ (e.g., δb, δl, or δd) is effected by decreasing each δ in the set (i.e., [δb, δl, or δd]) by the predefined value "d" (e.g., 1); thus, δ=δ−d (where δ refers to the entire set [δb, δl, or δd]).

If, on the other hand, the number of hypoglycemic events stored in the memory is insignificant, it may be necessary to increase δ in one or more of the set (i.e., [δb, δl, or δd]). To determine if an increase is due, the algorithm looks for an unbalanced response to insulin between the three meals (b, l, d). A patient's response to his/her recent short-acting insulin dosage is considered unbalanced if the mean blood-glucose-level measurements associated with two of the three meals falls within a predefined acceptable range (e.g., $>\alpha_1$ but $<\alpha_2$; where, for instance, $\alpha_1=80$ and $\alpha_2=120$), while the mean of the blood-glucose-level measurements associated with the third meal falls above the predefined acceptable range.

If the mean for two meals falls within [$\alpha_1$, $\alpha_2$], while the mean of the third meal is $>\alpha_2$, then the δ values for the updated set [δb, δl, or δd] are defined by the following, exemplary formulas:

$$\delta_{tmp}=\delta;$$

$$\delta_{tmp}(i)=\delta_{tmp}(i)+d;$$

If $(R_{\delta\text{-}tmp}<=R_\delta)$ or $(R_{\delta\text{-}tmp}<=D)$, then $\delta=\delta_{tmp}$ According to the foregoing, a test set of [δb, δl, or δd], designated $\delta_{tmp}$, is defined, wherein the value of each of δb, δl, and δd equals the present value of each corresponding δb, δl, and δd. The δ value in the test set corresponding to the meal (b, l, or d) where the blood-glucose-level measurement was determined to exceed the predefined acceptable range (e.g., $>\alpha_2$) is then increased by the value "d" (e.g., 1), and the new set is accepted if it complies with one of the statements: $R_{\delta\text{-}tmp}<=R_\delta$ (i.e., is the range $R_\delta$ of the test set ("$R_{\delta\text{-}tmp}$") less than or equal to the range ($R_\delta$) of the present set; or $R_{\delta\text{-}tmp}<=D$ (i.e., is the range $R_\delta$ of the test set ("$R_{\delta\text{-}tmp}$") less than or equal to the predefined value "D" (e.g., 2).

The foregoing will thus yield an increase in the insulin dosage for a particular meal if the patient's mean blood-glucose-level measurement data are outside of a predetermined range, such as, by way of example only, between $\alpha_1=80$ and $\alpha_2=120$.

Further according to this step 500, the binary hypoglycemic correction-flag is reset to 0, reflecting that the patient's insulin dosage regimen has been updated (and thus may be updated again at the next evaluation).

It will be appreciated that the PGR and CHR values determined at step 500 may optionally be employed by the processor to calculate, per conventional formulas, a "sliding scale"-type insulin dosage regimen. Such calculations may employ as a basis therefor a predefined average number of carbohydrates for each meal. Alternatively, data corresponding to such information may be input into the memory by the patient using data entry means.

Per the exemplary algorithm as described above, it will be appreciated that if a hypoglycemic event causes some dosage reduction, no other dosage can go up at the next update cycle.

It should be noted that, according to the exemplary embodiment of the algorithm herein described, any time a periodic evaluation of the patient insulin dosage regimen is undertaken, the algorithm treats the insulin dosage regimen as having been updated even if there has been no change made to the immediately preceding insulin dosage regimen. And, moreover, any time the insulin dosage regimen is updated, whether in consequence of a periodic update evaluation or an asynchronous update, the timer counting to the next periodic update evaluation will be reset to zero.

As noted, in operation of the invention according to any of the several embodiments as described herein there is initially specified by a healthcare professional a patient insulin dosage regimen comprised of, for example, a long-acting insulin dose component, a carbohydrate ratio component and a plasma-glucose correction factor component. This insulin dosage regimen data is entered in the memory of an apparatus, such as by a healthcare professional, in the first instance and before the patient has made any use of the apparatus. Optionally, and as necessary, the internal clock of the apparatus is set for the correct time for the time zone where the patient resides so that the time tags assigned to patient's blood-glucose-level measurements as they are subsequently input into the apparatus are accurate in relation to when, in fact, the data are input (whether automatically, manually, or a combination of both). Thereafter, the patient will input, or there will otherwise automatically be input (such as by the glucose meter) into the memory at least data corresponding to each successive one of the patient's blood-glucose-level measurements. Upon the input of such data, the processor determines, such as via the algorithm described hereinabove, whether and by how much to vary the patient's present insulin dosage regimen. Information corresponding to this present insulin dosage regimen is then provided to the patient so that he/she may adjust the amount of insulin they administer.

The foregoing description of the exemplary embodiments of the invention has been presented for purposes of illustration and description. They are not intended to be exhaustive of, or to limit the invention to, the precise forms disclosed, and modifications and variations thereof are possible in light of the above teachings or may be acquired from practice of the invention. The illustrated embodiments are shown and described in order to explain the principals of the innovation and its practical application to enable one skilled in the art to utilize the innovation in these and various additional embodiments and with various modifications as are suited to the particular use contemplated. Although only a few exemplary embodiments of the present innovations have been described in detail in this disclosure, those skilled in the art who review this disclosure will readily appreciate that many modifications are possible without materially departing from the novel teachings and advantages of the subject matter herein recited. Accordingly, all such modifications are intended to be included within the scope of the present innovations. Other substitutions, modifications, changes and omissions may be made in the design, operating conditions and arrangement of the exemplary embodiments without departing from the spirit of the present invention.

The invention in which an exclusive property or privilege is claimed is defined as follows:

1. An apparatus for improving a patient's insulin dosage regimen, comprising:
   at least one computer-readable memory for storing: programming instructions, data inputs corresponding at least to one or more components in the patient's insulin dosage regimen, and a patient's blood-glucose-level measurements determined at a plurality of times within a predefined period of time;
   a timer for monitoring the predefined period of time, the timer being incremented based on at least one of: passage of a separate predetermined increment of time or receipt of at least one of the patient's of blood-glucose-level measurements;
   a display operative to display information corresponding to at least the patient's insulin dosage regimen; and
   a processor configured to communicate with the at least one computer-readable memory and to execute the programming instructions stored in the at least one computer-readable memory to cause the apparatus to perform a method comprising:

(i) determining a number that represents excessive hypoglycemic events within the predefined period of time;
(ii) determining, after obtaining at least one blood-glucose-level measurement but before obtaining a subsequent blood-glucose-level measurement, whether the obtained blood-glucose-level measurement reflects a hypoglycemic event or a severe hypoglycemic event;
(iii) reducing at least one of the one or more components in the patient's insulin dosage regimen in response to a determination that the obtained blood-glucose-level measurement represents a severe hypoglycemic event;
(iv) reducing at least one of the one or more components in the patient's insulin dosage regimen in response to a determination that the obtained blood-glucose-level measurements results in an excessive number of hypoglycemic events during the predefined period of time; wherein the timer is reinitiated after the determination that there have been an excessive number of hypoglycemic events over the predefined period of time; and
(v) determining, at the end of the predefined period of time, from a plurality of the data corresponding to the patient's blood-glucose-level measurements whether and by how much to vary at least one of the one or more components in the patient's insulin dosage regimen in order to maintain the patient's blood-glucose-level measurements within a predefined range; and
(vi) communicating the revised at least one of the one or more components in the patients insulin dosage regimen to the display to enable the patient's insulin dosage regimen to be updated on the display;
wherein the timer is reinitiated after the determination of whether and by how much to vary at least one of the one or more components in the patient's insulin dosage regimen.

2. The apparatus of claim 1, further comprising data entry means for entering into the at least one computer-readable memory the data inputs corresponding to at least one of the one or more components of the patient's present insulin dosage regimen, the data entry means operatively connected to the computer-readable memory.

3. The apparatus of claim 1, further comprising a glucose meter operative to provide to the at least one computer-readable memory the data inputs corresponding at least to the patient's blood-glucose-level measurements determined at a plurality of times.

4. The apparatus of claim 3, further comprising data entry means for entering into the at least one computer-readable memory the data inputs corresponding to at least one of the one or more components of the patient's present insulin dosage regimen.

5. The apparatus of claim 3, wherein the processor is operative to associate with the data inputs corresponding at least to the patient's blood-glucose-level measurements determined at a plurality of times an identifier indicative of when the measurement was input into the memory.

6. The apparatus of claim 5, further comprising data entry means enabling a user to define the identifier associated with each blood-glucose-level measurement data-input.

7. The apparatus of claim 5, further comprising data entry means enabling a user to confirm the correctness of the identifier associated with each blood-glucose-level measurement data-input.

8. The apparatus of claim 5, further comprising data entry means enabling a user to modify the identifier associated with each blood-glucose-level measurement data-input.

9. The apparatus of claim 1, further comprising an insulin pump operatively connected to the processor, the insulin pump operative to deliver insulin to a patient according to the patient's present insulin dosage regimen.

10. The apparatus of claim 9, further comprising data entry means for entering into the at least one computer-readable memory the data inputs corresponding to at least one of the one or more components of the patient's present insulin dosage regimen, the data entry means operatively connected to the computer-readable memory.

11. The apparatus of claim 9, further comprising a glucose meter operative to provide to the at least one computer-readable memory the data inputs corresponding at least to the patient's blood-glucose-level measurements determined at a plurality of times.

12. The apparatus of claim 11, further comprising data entry means for entering into the at least one computer-readable memory the data inputs corresponding to at least one of the one or more components of the patient's present insulin dosage regimen.

13. The apparatus of claim 11, wherein processor is operative to associate with the data inputs corresponding at least to the patient's blood-glucose-level measurements determined at a plurality of times an identifier indicative of when the measurement was input into the memory.

14. The apparatus of claim 13, further comprising data entry means enabling a user to define the identifier associated with each blood-glucose-level measurement data-input.

15. The apparatus of claim 13, further comprising data entry means enabling a user to confirm the correctness of the identifier associated with each blood-glucose-level measurement data-input.

16. The apparatus of claim 13, further comprising data entry means enabling a user to modify the identifier associated with each blood-glucose-level measurement data-input.

17. The apparatus of claim 10, wherein the data inputs further comprise data inputs corresponding to the patient's weight, and the data entry means facilitate entering into the at least first memory the data inputs corresponding to the patient's weight.

18. The apparatus of claim 10, wherein the data inputs further comprise data inputs corresponding to the foods consumed by a patient, the data entry means facilitate entering into the at least first memory data inputs corresponding to the foods consumed by a patient, and the processor is operative to determine from the data inputs corresponding to the foods consumed by a patient the number of carbohydrates associated those foods.

19. The apparatus of claim 10, wherein the data inputs further comprise data inputs corresponding to the number of insulin units administered by a patient on a periodic basis, and the data entry means facilitate entering into the at least one computer-readable memory inputs corresponding to the said number of insulin units administered by a patient.

20. The apparatus of claim 9, wherein the insulin pump is operative to provide to the at least one computer-readable memory data inputs corresponding to the rate at which insulin is delivered to the patient by the pump according to the patient's present insulin dosage regimen.

21. The apparatus of claim 2, wherein the data inputs further comprise data inputs corresponding to the patient's weight, and the data entry means facilitate entering into the at least first memory the data inputs corresponding to the patient's weight.

22. The apparatus of claim 2, wherein the data inputs further comprise data inputs corresponding to the foods consumed by a patient, the data entry means facilitate entering into the at least first memory data inputs corresponding to the foods consumed by a patient, and the processor is operative to determine from the data inputs corresponding to the foods consumed by a patient.

23. The apparatus of claim 2, wherein the data inputs further comprise data inputs corresponding to the number of insulin units administered by a patient on a periodic basis, and the data entry means facilitate entering into the at least one computer-readable memory data inputs corresponding to the said number of insulin units administered by a patient.

\* \* \* \* \*